(12) United States Patent
Holtzapple et al.

US008765429B2

(10) Patent No.: US 8,765,429 B2
(45) Date of Patent: Jul. 1, 2014

(54) BIOMASS SHOCK PRETREATMENT

(75) Inventors: Mark T. Holtzapple, College Station, TX (US); Maxine Jones Madison, Houston, TX (US); Rocio Sierra Ramirez, Bogotá (CO); Mark A Deimund, Oklahoma City, OK (US); Matthew Falls, Whippany, NJ (US); John J. Dunkleman, Somerville, TX (US)

(73) Assignee: The Texas A & M University System, College Station, TX (US)

( * ) Notice: Subject to any disclaimer, the term of this patent is extended or adjusted under 35 U.S.C. 154(b) by 0 days.

(21) Appl. No.: 13/433,089

(22) Filed: Mar. 28, 2012

(65) Prior Publication Data
US 2012/0252070 A1    Oct. 4, 2012

Related U.S. Application Data

(60) Provisional application No. 61/468,380, filed on Mar. 28, 2011.

(51) Int. Cl.
*C12P 7/10*        (2006.01)
(52) U.S. Cl.
USPC ........... 435/165; 435/151; 435/161; 102/200; 530/500
(58) Field of Classification Search
USPC ......................................................... 530/500
See application file for complete search history.

(56) References Cited

U.S. PATENT DOCUMENTS

| 4,248,972 | A | * | 2/1981 | Fischer et al. | ............. | 435/294.1 |
| 5,865,898 | A | * | 2/1999 | Holtzapple et al. | ............. | 127/37 |
| 6,043,392 | A | | 3/2000 | Holtzapple et al. | | |
| 6,262,313 | B1 | | 7/2001 | Holtzapple et al. | | |
| 6,395,926 | B1 | | 5/2002 | Holtzapple et al. | | |
| 7,244,459 | B2 | | 7/2007 | Long et al. | | |
| 8,362,306 | B2 | | 1/2013 | Wheeler et al. | | |
| 2008/0311638 | A1 | * | 12/2008 | Navapanich et al. | ......... | 435/165 |

FOREIGN PATENT DOCUMENTS

KR         10-0325414 B1      2/2002

OTHER PUBLICATIONS

Holt et al. "Compact Marx Generators Modified for Fast Risetime" (2009) IEEE: Pulsed Power Conference, 1197-1200.*
Xiong et al. "Exoplosion Shock Separation: A New Approach in Pretreatment Technique of Lignocellulosic Materials" (1998) International Society of Explosives Engineers, vol. 24th: 263-271.*
Mosier et al. "Features of promising technologies for pretreatment of lignocellulosic biomass" (2005) Bioresource Technology vol. 96, 673-686.*
Troit et al. "Design of Explosion Blast Containment Vessels for Explosive Ordnance Disposal Units" (1975) DOD Contract (1 No. DAAA21-72-C-0129, 117 pages.*
Krishnan et al. "Alkali-Based AFEX Pretreatment for the Converstion of Sugarcane Bagasse and Cane Leaf Residues to Ethanol," Biotechnology and Bioengineering; vol. 107; No. 3; dated Oct. 2010; pp. 441-450 (10 pgs.).
Zheng et al. "Pretreatment for Cellulose Hydrolysis by Carbon Dioxide Explosion," Biotechnology Prog.; vol. 14; dated 1998; pp. 890-896 (7 pgs.).
Sun et al. "Hydrolysis of Lignocellulosic Materials for Ethanol Production: a Review," Bioresource Technology; vol. 83; dated 2002; pp. 1-11 (11 pgs.).
Falls et al. "Investigation of Shock Treatment on Lime Pretreated Biomass," MS Thesis; Texas A&M University; College Station, TX; dated 2011 (47 pgs.).
Raloff, Janet "A Shocking Science to Tender Poultry," Food Science; dated Jan. 9, 2003 (2 pgs.).
Raloff, Janet "A Shockingly Unconventional Meat Tenderizer," Science News; vol. 153; No. 23; dated Jun. 6, 1998 (6 pgs.).
Bhaskaran et al. "The Shock Tube as Wave Reactor for Kinetic Studies and Material Systems," Progress in Energy and Combustion Science; vol. 28; p. 151-192; dated 2002 (42 pgs.).
Falls et al. "Mechanical Pretreatment of Biomass—Part II: Shock Treatment" MS Thesis; Texas A&M University; College Station, TX; dated 2011 (37 pgs.).
Jones, Maxine "Effects of Physical and Chemical Pretreatments on the Crystallinity of Bagasse," MS Thesis; Texas A&M University, College Station, TX; dated 2007 (200 pgs.).
Zhu et al. Structural Features Affecting Biomass Enzymatic Digestibility, Bioresource Technology; vol. 99; No. 9; pp. 3817-3828; dated 2008 (12 pgs.).
Chang et al. "Fundamental Factors Affecting Biomass Enzymatic Reactivity," Applied Biochemistry and Biotechnology; vol. 84-86; pp. 5-37; dated 2000 (33 pgs.).
Maiorella et al. "By-Product Inhibition Effects on Ethanolic Fermentation by *Saccharomyces cerevisiae*," Biotechnology and Bioengineering; vol. 25; pp. 103-121; dated 1983 (19 pgs.).
Zhu et al. "Multiple Linear Regression Model for Predicting Biomass Digestibility from Structural Features," Bioresource Technology; vol. 101; No. 13; p. 4971-4979; dated 2010 (9 pgs.).
Falls et al. "Investigation of Enzyme Formulation on Pretreated Switchgrass," Bioresource Technology; vol. 102; No. 24; pp. 11072-11079; dated 2011 (8 pgs.).
Inoue et al. "Combining Hot-Compressed Water and Ball Milling Pretreatments to Improve the Efficiency of the Enzymatic Hydrolysis of Eucalyptus," Biotechnology for Biofuels; vol. 1; No. 2; dated Apr. 15, 2008 (9 pgs.).

(Continued)

*Primary Examiner* — Jon P Weber
*Assistant Examiner* — Teresa E Knight
(74) *Attorney, Agent, or Firm* — Timothy S. Westby; Porter Hedges, LLP

(57) ABSTRACT

Methods and apparatus for treating biomass that may include introducing a biomass to a chamber; exposing the biomass in the chamber to a shock event to produce a shocked biomass; and transferring the shocked biomass from the chamber. In some aspects, the method may include pretreating the biomass with a chemical before introducing the biomass to the chamber and/or after transferring shocked biomass from the chamber.

19 Claims, 18 Drawing Sheets

(56) References Cited

OTHER PUBLICATIONS

Falls et al. "Development of Shock Treatment as a Novel Mechanical Biomass Pretreatment Process," in Preparation; Department of Chemical Engineering at Texas A&M University; Annual Report; dated Mar. 13, 2012 (31 pgs.).
Meysing, Daniel "Investigations of Biomass Pretreatment and Submerged Fixed-Bed Fermentation," MS Thesis, Texas A&M University, College Station, TX; dated 2011 (157 pgs.).
Granda et al. "Low-Pressure Sugar Extraction With Screw-Press Conveyors," International Sugar Journal; vol. 108; No. 1294; dated 2006 (8 pgs.).
Meysing et al. "Conversion of Biomass to Mixed Acids: Oxidative Lime and Shock Tube Pretreatment and Mixed-Acid Fermentation," Lambert Academic Publishing; dated 2012 (141 pgs.).
Kabir et al. "Techno-Economic Analysis of Biochemical Scenarios for Production of Cellulosic Ethanol," Technical Report; NREL/TP-6A2-46588; dated Jun. 2010 (102 pgs.).
Templeton et al. "Compositional Analysis of Lignocellulosic Feedstocks. 2. Method Uncertainties," J. Agric Food Chem; vol. 58; pp. 9054-9062; dated 2010 (9 pgs.).
Selig et al. Enzymatic Saccharification of Lignocellulosic Biomass, Laboratory Analytical Procedure, Technical Report; NREL/TP-510-42629; dated Mar. 2008 (8 pgs.).
Kim et al. "Lime Pretreatment and Enzymatic Hydrolysis of Corn Stover," Bioresource Technology; vol. 96; pp. 1994-2006; Special Issue dated May 2004 (237 pgs.).
Chang et al. "Lime Pretreatment of Switchgrass," Applied Biochemistry and Biotechnology, vol. 63-65; pp. 3-19; dated 1997 (17 pgs.).
Lara et al. An Investigation of High Operating Temperatures in Mechanical Vapor-Compression Desalination; Desalination 227; pp. 217-232; dated 2008 (16 pgs.).
Tao et al. "Process and Technoeconomic Analysis of Leading Pretreatment Technologies for Lignocellulosic Ethanol Production Using Switchgrass," Bioresource Technology; vol. 102; No. 24; pp. 11105-11114; dated 2011 (10 pgs.).
AccelleraseTrio "Optimized Cellulase, Hemicellulase and Beta-Glucosidase Enzyme Complex for Improved Lignocellulosic Biomass Hydrolysis," Genencor: A Danisco Division; dated 2011 (4 pgs.).
Falls et al. "Development of Highly Digestible Animal Feed From Forage Sorghum and Corn Stover" in Preparation; Department of Animal Science; Texas A&M University; dated Aug. 2006 (38 pgs.).
Falls, Matthew D. "Development of Oxidative Lime Pretreatment and Shock Treatment to Produce Highly Digestible Lignocellulose for Biofuel and Ruminant Feed Applications," MS Thesis; Texas A&M University; College Station, TX; dated 2011 (270 pgs.).
Madison et al. "Mechanical Pretreatment of Biomass—Part I: Acoustic and Hydrodynamic Cavitation," MS Thesis; Texas A&M University; College Station, TX; dated 2011 (32 pgs.).
International Preliminary Report on Patentability dated Oct. 10, 2013 for corresponding International Application No. PCT/US2012/030998 (6 pgs.).
Search Report and Written Opinion dated Oct. 31, 2012 for corresponding International Application No. PCT/US2012/030998 (9 pgs.).

\* cited by examiner

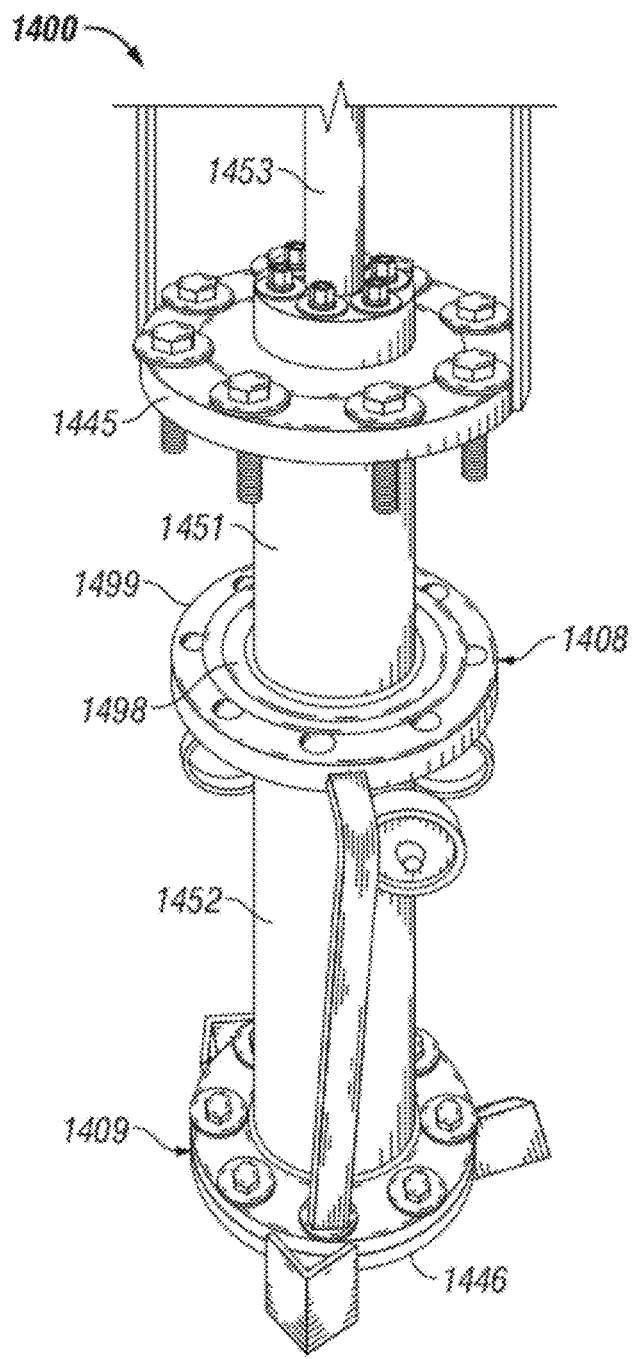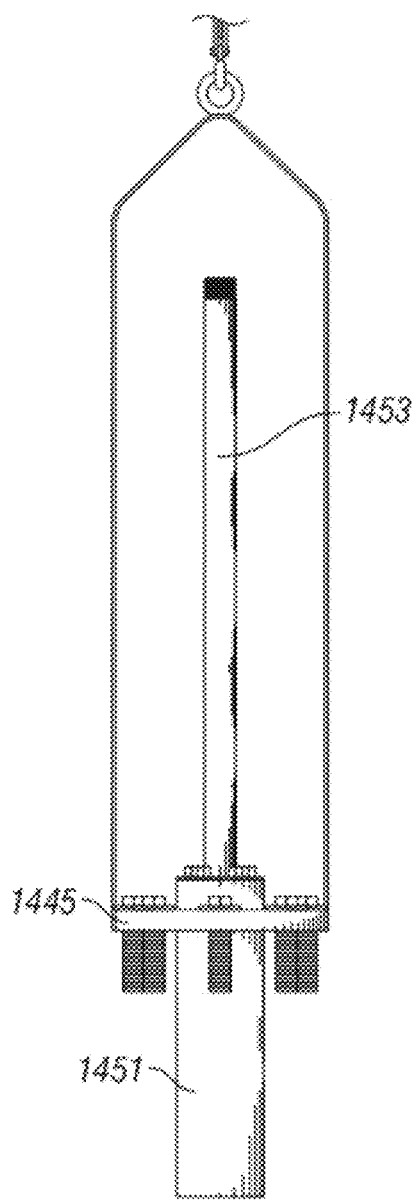
FIG. 14A
FIG. 14B

BIOMASS SHOCK PRETREATMENT

STATEMENT REGARDING FEDERALLY SPONSORED RESEARCH OR DEVELOPMENT

This invention was made with government support under DOE A1380 awarded by the U.S. Department of Energy. The government has certain rights in the invention.

CROSS-REFERENCE TO RELATED APPLICATIONS

This application claims the benefit under 35 U.S.C. §119(e) of U.S. Provisional Patent Application No. 61/468,380 filed Mar. 28, 2011, the disclosure of which is hereby incorporated herein by reference.

BACKGROUND

1. Field of the Disclosure

Embodiments disclosed herein relate to methods for enhancing the digestibility of biomass (e.g., lignocellulose, grains) using shock treatment. Additionally, shock treatment can be used to improve meat tenderness. Specific embodiments pertain to degradation of lignocellulosic biomass material as a result of a shock treatment applied thereagainst.

2. Background of the Disclosure

In the biomass industry, the biological production of useful products from biomass is significantly hindered by the slow and incomplete hydrolysis of biomass, particularly high-lignin biomass. Digestibility is limited because of the presence of chemical components (e.g., lignin) and structural features (e.g., inaccessible surface area, crystallinity).

Chemical pretreatment is a known method of lignin removal, but it may not significantly affect structural features. Physical treatments like ball milling and two-roll milling are known to affect structural features; however, they are cost prohibitive and not economically feasible for an industrial process.

For commercial viability, when converting biomass (e.g., lignocellulose, grain) to useful products (e.g., animal feed, biofuels), there is a critical need to enhance pretreatment, which improves both the rate and extent of conversion. Although many chemical treatments are commercially viable, there are very few physical treatments that are economical and effective. As such, there is a critical need for an economically viable and effective physical pretreatment of biomass. Further, there is a need to supplement chemical pretreatment processes to further increase digestibility of biomass.

Meat tenderization is another important issue. For example, grass-fed beef is more healthful than grain-fed beef; however, grass-fed beef is not as tender, which reduces its palatability. Although extensive aging can improve the tenderness of grass-fed beef, this is expensive; thus, there is a need for a rapid method to improve meat tenderness.

There is a further need for reducing cycle and process time with an ability to quickly load and unload a shock vessel or apparatus.

SUMMARY

This disclosure relates to apparatuses and methods for enhancing the digestibility of biomass using shock treatment. In this disclosure, "biomass" may be any material derived from a living organism. In non-limiting examples, the biomass may be plant material including leaves, stems, roots, grains, beans, legumes, and other plant components. The digestion of plant material can occur by both biological (e.g., enzymes) and chemical (e.g., acid) means. Embodiments disclosed herein pertain to shock-treatment of biomass to enhance the extent and rate of digestion, which has industrial advantages for both the production of industrial fuels and chemicals, as well as production of animal feed. Additionally, "biomass" can refer to material derived from animals, such as meat. This disclosure relates to apparatuses and methods for enhancing the tenderness of meat protein.

In conjunction with embodiments of the present disclosure, a "shock" may be considered a mechanical or physical effect that results from sudden acceleration or deceleration caused by an event (e.g., an explosion). "Shock" in the sense of the present disclosure may also be considered a transient physical excitation.

Examples of transient physical excitation may result from a 'shock' wave, pressure wave, pressure pulse, etc. generated form a source or event, such as an explosion. In a non-limiting example, 'shock' may be considered a mechanical pretreatment that subjects biomass to a rapid pressure pulse, which disrupts the biomass structure rendering it more susceptible to enzymatic digestion. "Shock," "shock treatment," "shock(ed) biomass," "shock effect," etc. all have related meanings within this context in the sense they are referring to the description and definition provided herein. Words and/or phrases pertaining to shock (e.g., "shock" and "shock treatment") may be used interchangeably without limitation, unless so indicated.

Embodiments disclosed herein pertain to a method of biomass pretreatment that may include the steps of introducing a biomass to a chamber; exposing the biomass in the chamber to a shock event to produce a shocked biomass; and transferring the shocked biomass from the chamber. In some aspects, the method may include pretreating the biomass with a chemical before introducing the biomass to the chamber. In other aspects, the method may include pretreating the shocked biomass with a chemical after transferring the shocked biomass from the chamber. The chemical may be an ash material.

The method may include feeding a gaseous mixture to the chamber; and igniting the gaseous mixture in the chamber. The method may alternatively include adding an explosive material to the chamber; and detonating the explosive material in the chamber.

The chamber may include a first end and a second end, each end having an end cap or cover movably attached thereto. One or more of the covers may include a sloped surface configured to assist in rapid opening, closing, and sealing of the covers with the ends. In some aspects, the shocked biomass may be transferred from the chamber by opening the second end and gravitational force.

Other embodiments disclosed herein pertain to a method of biomass pretreatment that may include the steps of introducing a lignin-based biomass to a high-pressure vessel; exposing the biomass in the high-pressure vessel to a shock wave to produce a shocked biomass; and transferring the shocked biomass from the high-pressure vessel. In embodiments, the shock wave may result from a pressure increase of at least 100 psi in less than 1 second of elapsed time.

Other aspects of the method may include pretreating the lignin-based biomass prior to introduction into the chamber by adding calcium oxide or hydroxide, water, and an oxidizing agent to the biomass to form a slurry mixture; and oxidizing lignin in the slurry mixture while maintaining the mixture at greater than ambient temperature.

Yet other embodiments of the disclosure pertain to a method for enhancing biomass digestibility using shock treatment. The method may include pretreating a lignin-based biomass with a chemical to produce a pretreated biomass; introducing the pretreated biomass to a high-pressure vessel; exposing the biomass to a shock event to produce a shocked biomass; and transferring the shocked biomass from the high-pressure vessel.

In addition, the method may include countercurrently washing at least a portion of the shocked biomass with water; and forming a biomass slurry with the wash water and the pretreated biomass. In some aspects, chemical may be one of an alkali material, an ash material, or combinations thereof. The shock event may include a pressure increase of at least 100 psi in less than 1 second.

The high-pressure vessel may include a first end and a second end, and each end may include an end cap or a cover movably attached thereto. One or more of the end caps may include a sloped surface configured to assist in rapid opening, closing, and sealing of the covers with the ends. The shocked biomass may be transferred from the high-pressure vessel from opening the second end and gravitational pull.

Yet other embodiments disclosed herein pertain to a shock apparatus configured for rapid transfer of a biomass to and therefrom. The shock apparatus may include a main body comprising a chamber, a first end, and a second end, wherein the chamber is configured for the biomass transferred therein to be subjected to a shock; a first end cap movably associated with the first end, and a second end cap movably associated with the second end; a frame for holding the main body in a predetermined orientation; a first actuator coupled with the frame, the first actuator configured for opening and closing the first end cap; and a first clamp coupled with the frame, the first clamp being operable to hold the first end cap in a sealingly engaged position with the first end.

The shock apparatus may also include a second actuator coupled with the frame. The second actuator may be configured for opening and closing the second end cap. There may be a second clamp coupled with the frame. The second clamp may be operable to hold the second end cap in a sealingly engaged position with the second end. In some aspects, the predetermined position may be along a vertical axis with respect to an earthen surface.

The shock tube apparatus may include an additional first clamp coupled with the frame, the additional first clamp being operable to hold the first end cap in a sealingly engaged position with the first end; and an additional second clamp coupled with the frame, the additional second clamp being operable to hold the second end cap in a sealingly engaged position with the second end, wherein the biomass is lignin-based or grain-based.

The shock tube apparatus may include the first actuator, the second actuator, the first clamp, and the second clamp are each separately operable with a movable piston. In some aspects, each of the movable pistons may be pneumatically, hydraulically, or electrically actuated.

The first end cap may include a first sloped surface, and the second end cap may include a second sloped surface. Engagement between the first clamp, the first sloped surface, and the main body may result in compression therebetween. In addition, engagement between the second clamp, the second sloped surface, and the main body may also result in compression therebetween.

The biomass may be transferred to the apparatus through the first end. The shock event may include a time elapse of less than 1 second, and a pressure increase of at least 100 psi. In an embodiment, the shock event may result from ignition of a gaseous mixture fed into the chamber. The biomass may be grain-based or lignin-based, and the shocked biomass may be transferred from the apparatus through the second end.

Still other embodiments of the disclosure pertain to a shock apparatus configured for rapid transfer of a biomass to and therefrom. The apparatus may include a main body comprising a chamber, a first end, and a second end, wherein the chamber is configured for the biomass transferred therein to be subjected to a shock; a first conical shaped end cap movably associated with the first end, and a second end cap movably associated with the second end; a frame for holding the main body in a predetermined orientation; a first actuator coupled with the frame, the first actuator configured for opening and closing the first conical end cap; and a first clamp coupled with the frame. The first clamp may be operable to hold the first conical end cap in a sealingly engaged position with the first end. The first conical shaped end cap may include a first sloped surface. Engagement between the first clamp, the first sloped surface, and the main body may result in compression therebetween.

Thus, embodiments described herein comprise a combination of features and advantages intended to address various shortcomings associated with certain prior devices. The various characteristics described above, as well as other features, will be readily apparent to those skilled in the art upon reading the following detailed description of the preferred embodiments, and by referring to the accompanying drawings.

BRIEF DESCRIPTION OF THE DRAWINGS

For a detailed description of the preferred embodiments of the invention, reference will now be made to the accompanying drawings in which:

FIGS. 14A-14D illustrate a shock tube apparatus with a barrel, according to an embodiment of the disclosure.

DETAILED DESCRIPTION OF THE PREFERRED EMBODIMENTS

Embodiments disclosed herein are directed to methods and apparatuses for shock-treatment of biomass in order to enhance its extent and rate of digestion with enzymes or acids. These methods and apparatuses may be rapid, inexpensive, and effective. Evidence shows shock treatment beneficially affects the physical structure of the biomass, and that enzymes have easier access to chemical bonds. Embodiments described may be applicable to any biomass material derived from a living organism; in non-limiting examples, the biomass may be plant material including leaves, stems, roots, grains, beans, legumes, and other plant components, and combinations thereof. Further, methods and apparatuses are described by which meat may be tenderized by shock treatment.

Figure 1C:
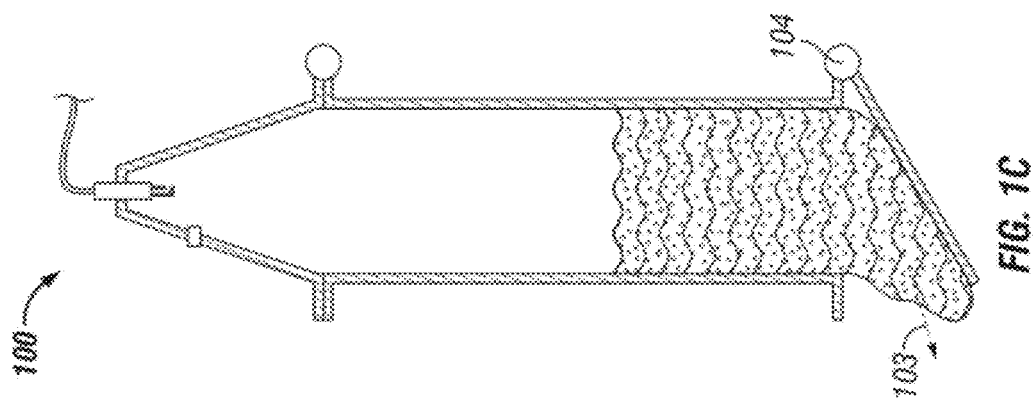
FIGS. 1A-1C illustrate a shock tube apparatus operable with a fill, shock, and dump cycle, according to an embodiment of the disclosure.
Figure 1B:
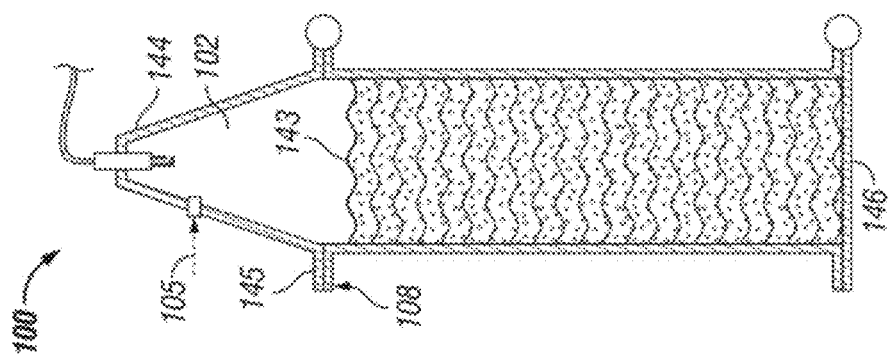
Figure 1A:
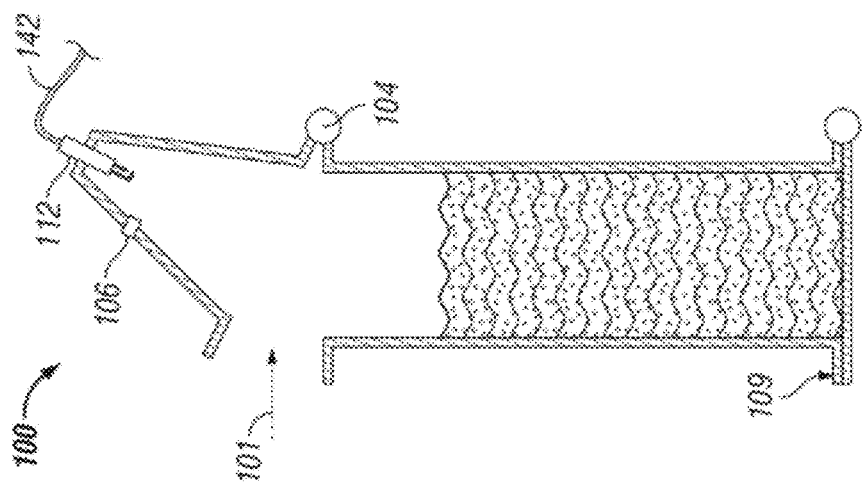

Referring now to FIGS. 1A-1C together, a shock tube apparatus operational with a fill, shock, and dump cycle, according to embodiments disclosed herein, is shown. FIGS. 1A-1C illustrate an example of the shock tube apparatus 100. Although the term 'tube' may be used for descriptive purposes, it is not meant to be limiting to any particular apparatus shape. Thus, apparatus 100 may be other shapes, such as oval, conical, square, modular, etc.

In an embodiment, apparatus 100 may be a cylindrical pipe or chamber with two end caps 145, 146 mateable on each end 108, 109, respectively. As shown, the upper and lower end caps 145, 146 may be connected with the apparatus 100 in a movable or rotatable fashion, such as with one or more hinges 104. In an embodiment, end caps 145 and/or 146 may be flanges connectable to the apparatus 100 via a flange connection. The ability to open and close the apparatus 100 provides for a biomass (e.g., lignocellulose such as sugarcane bagasse, starch-containing grains such as corn) or biomass slurry 101 to be rapidly added and removed therefrom. In some aspects, the upper cap 145 may include a conical shape portion attached therewith, whereas in other aspects the bottom cap 146 may be flat. In an embodiment, the biomass slurry 101 may be an aqueous slurry.

FIG. 1A shows a fill cycle where biomass slurry 101 may be introduced into the apparatus 100. After biomass slurry 101 is added to the shock apparatus 100, the end caps 145, 146 may be sealingly closed, thus creating an internal environment within the apparatus 100 that may be isolated from external surroundings. As shown in FIG. 1B, a head or vapor space 102 located above top liquid level 143 may be filled with gas 105. Gas may be introduced into the apparatus 100 via a fluid nozzle or inlet 106, as would be apparent to one of ordinary skill in the art. In an embodiment, the gas 105 may be a flammable gas (e.g., methane, hydrogen). In addition, the apparatus must also contain a suitable oxidant (e.g., air, oxygen).

Gas 105 may be a mixture of flammable gas combined with an oxidant, such as oxygen, air, etc. In operation, the gas mixture 105 may be ignited, such as with an igniter device 112. The igniter device 112 may be any ignition device apparent to one of skill in the art for igniting the gas mixture 105, such as a spark plug. In an embodiment, the igniter may be electrically connected with a power source (not shown) via wire 142. Upon ignition or activation, the igniter device 112 may create an arc or spark within the head space 102 of the apparatus. The igniter device 112 may be securely and sealingly held in place via a socket 144 (or other suitable device) disposed in the apparatus 100. Alternatively, an explosive, such as TNT, dynamite, gunpowder, etc. (not shown) may be disposed in the head space 102 and detonated. Detonation may occur via activation of a fuse or firing pin or the like.

After the shock treatment, the shocked biomass 103 may be removed or emptied from the apparatus 100, as shown in FIG. 1C, at which point any aspect of the cycle may be repeated as desired.

Figure 2C:
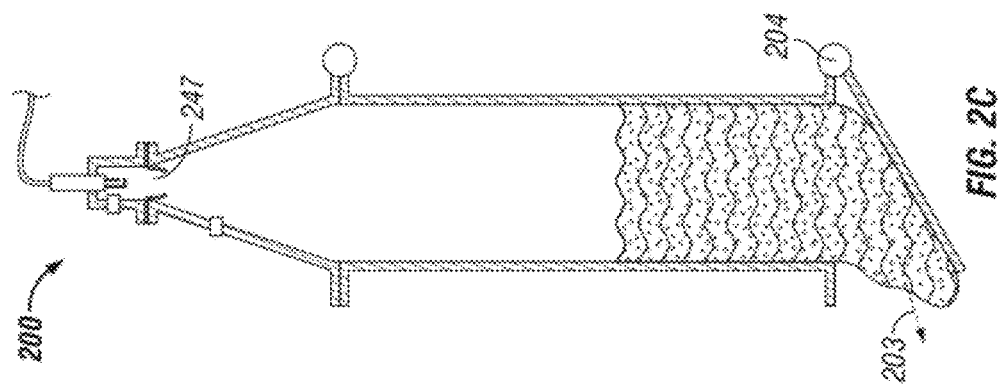
FIGS. 2A-2C illustrate a shock tube apparatus configured with an ignition chamber, and operable with a fill, shock, and dump cycle, according to an embodiment of the disclosure.
Figure 2B:
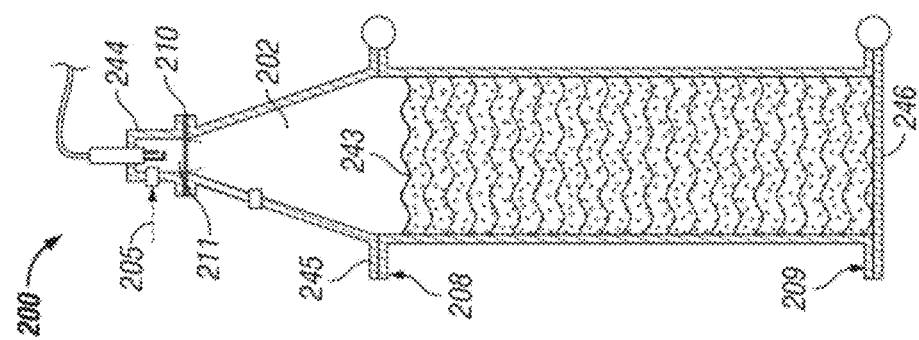
Figure 2A:
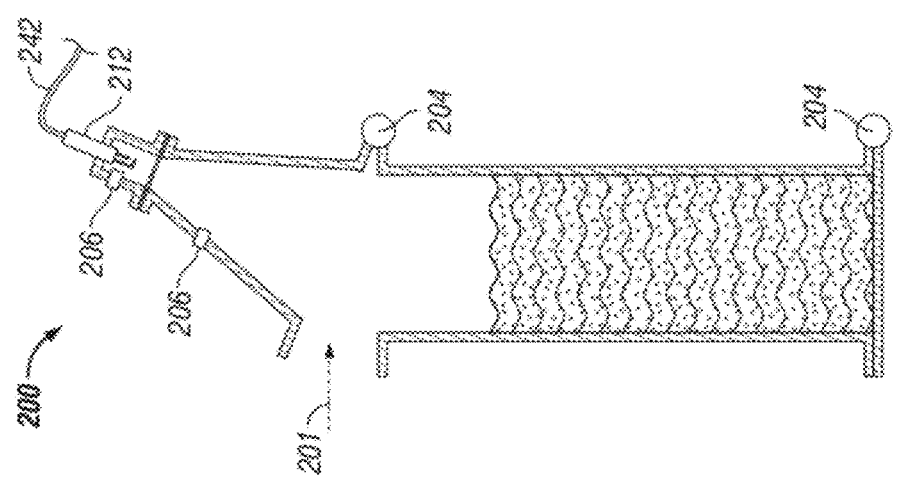

Referring now to FIGS. 2A-2C, a shock tube apparatus 200 configured with a rupture disk and an ignition chamber, and operational with a fill, shock, and dump cycle, according to embodiments disclosed herein, is shown. FIGS. 2A-2C show an example of a shock tube apparatus 200 that employs a rupture disk 210 and an ignition chamber 211. Like the apparatus 100 previously described, the apparatus 200 may be used for shock treatment of biomass.

The apparatus 200 may include similar components (or subcomponents) and materials of construction as described herein for other apparatuses, such that other shock apparatuses and apparatus 200 may be similar; however, any of the apparatuses disclosed are not necessarily identical. Moreover, it is within the grasp of one of skill that any of the apparatus embodiments described may be used within any of the methods and processes of the present disclosure, and vice versa.

In an embodiment, shock tube apparatus 200 may be a steel pipe in which a low-pressure gas and a high-pressure gas are separated by a rupture disk 210, diaphragm (not shown), or the like. The disk 210 may burst open under predetermined conditions, resulting in a shock wave in the apparatus 200 and against biomass 201. In an embodiment, the shock tube apparatus 200 of the present disclosure may be constructed of 4-in Schedule 80 steel pipe, and have one or more flanged ends. The apparatus 200 may be constructed with a maximum allowable pressure of about 2000 psi.

The apparatus 200 may be a cylindrical pipe or chamber with an end cap 245, 246 mateable to each end 208, 209 of the apparatus, respectively. In an embodiment, end caps 245 and/or 246 may be flanges connectable to the apparatus via a flange connection. As shown, the upper and lower end caps 245, 246 may be connected with the apparatus 200 in a pivoting manner with one or more hinges 204. FIG. 2A illustrates the fill cycle that includes introducing biomass 201 into the apparatus 200. After biomass slurry 201 is added to the shock apparatus 200, one or both of the end caps 245, 246 may be sealingly closed, thus creating an internal environment within the apparatus 200 that is isolated from external surroundings.

FIG. 2B illustrates how the shock cycle may commence once the slurry 201 is in the apparatus 200. Once the apparatus 200 is closed, a head or vapor space 202 may be filled with gas 205 in a like manner as previously described. For example, gas may be introduced into the apparatus 200 via a fluid nozzle or inlet 206. In operation, the gas mixture 205 may be ignited, such as with an igniter device 212. The igniter device may be any ignition device apparent to one of skill in the art for igniting the gas mixture 205, such as a spark plug. In an embodiment, the igniter may be electrically connected with a power source (not shown) via wire 242. Upon ignition or activation, the igniter device 212 may create an arc or spark within the head space 202 of the apparatus 200. The igniter device 212 may be securely and sealingly held in place via a socket 244 (or other device) disposed in the apparatus 200.

In the embodiment depicted, gas 205 or explosive (not shown) may initially be added to an ignition chamber 211 closed off by a rupture disk 210 (or other suitable isolation device). If an explosive is used, detonation may occur via activation of fuse, firing pin, or other suitable detonator.

When the pressure in the chamber 211 exceeds the capacity of the rupture disk 210, the disk 210 may rupture (i.e., rupture 247), and the gas 205 in the chamber may then shock the contents of the shock tube apparatus 200. After the shock, the shocked biomass 203 may be removed or emptied from the apparatus 200, as shown in FIG. 2C, at which point any aspect of the shock cycle may be repeated as desired.

Figure 3:
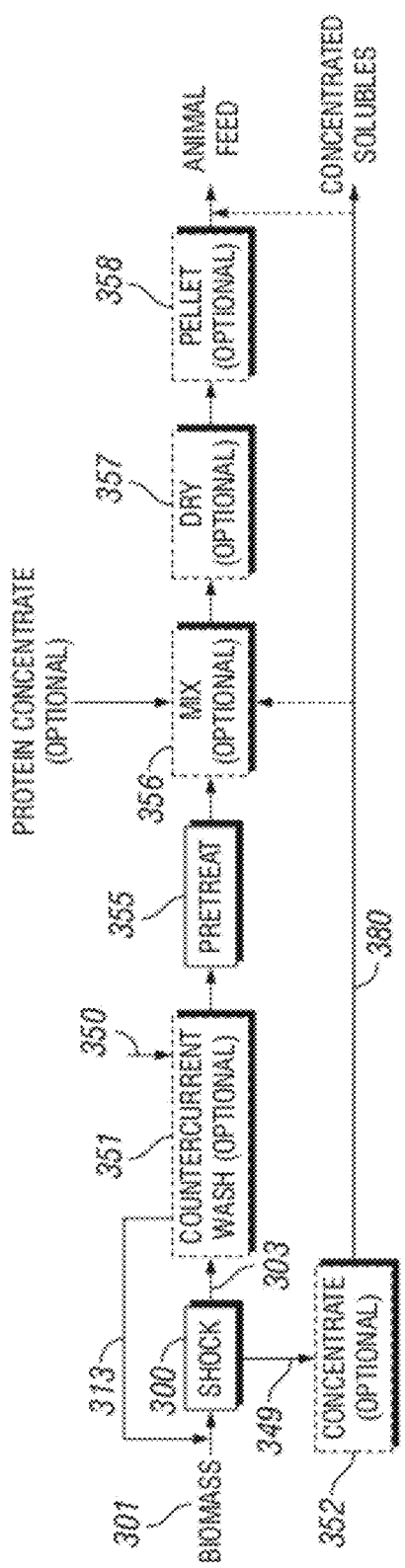
FIGS. 3 and 4 illustrate a block flow diagram for a process of making animal feed with shock and pretreat conditions, according to an embodiment of the disclosure.
Figure 4:
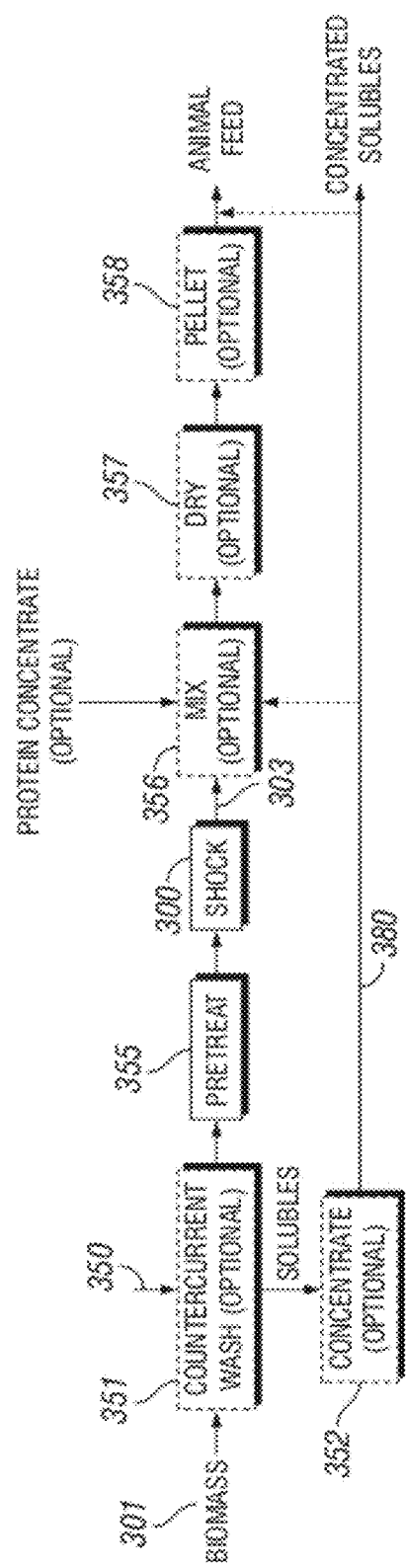

Referring now to FIGS. 3 and 4 together, a process for converting biomass into animal feed, according to embodiments disclosed herein, is shown. Biomass slurry 301 may be exposed to shock treatment 300, such as in a shock tube apparatus (e.g., 100, FIG. 1). In an embodiment, the shocked biomass 303 may contain significant amounts of solubles, and it may be desired to separate the solubles from the shocked biomass 303. As such, the shocked biomass 303 may be washed with a wash liquid 350, such as with water. In an embodiment, the shocked biomass 303 may be countercurrently washed 351 in a wash vessel (not shown). The resultant wash water stream 313 may be used as a source of liquid for forming the biomass feed slurry 301. The soluble includes biomass components, such as free sugars, soluble oligosaccharides, proteins, ash, and other biomass components, many of which are valuable components of animal feed because they are readily digested.

In other aspects, the shock tube apparatus may have liquid 349 exiting therefrom which may be treated to drying or other suitable liquid-removal unit operation. For example, with the presence of liquid such as water, the water may be removed in a concentration step, such as with reverse osmosis, multi-effect evaporators, vapor-compression distillation, and the like, as would be apparent and understood to one or ordinary skill in the art. In other aspects, the use of drying may result in concentrated solubles 380. Concentrated solubles 380 may be, for example, sold as an animal feed and/or optionally blended 356 in with the shock product.

Before or after shock 300, or after the optional washing 351, the biomass 301 or 303 may be pretreated using any one of a variety of pretreatments 355 known to one of skill in the art. Pretreatment may include physical and/or chemical aspects, such as ball milling or application of an alkali material, or combinations of each.

Further non-limiting examples of chemical pretreatments may include, but are not limited to, AFEX (Ammonia Fiber Expansion), ARP (Ammonia Recycle Percolation), steam explosion, carbon dioxide explosion, dilute acid, autohydrolysis, neutral high-temperature water, alkali, alkali+air, alkali+oxygen, organosolv, and combinations thereof. Any pretreatment(s) steps may be used in accordance with any of the methods and apparatus disclosed herein, as would be apparent to one of ordinary skill in the art.

Pretreatment 355 may be used, for example, to remove lignin, or to render the lignin in such a form that it does not hinder enzyme access to desired portions of the biomass, such as cellulose and hemicellulose.

Examples of Pretreatment Conditions
1. Lime only
Lime loading=0.05 to 0.4 g $Ca(OH)_2$/g biomass
Time=1 to 24 h
Temperature=60 to 140° C.
2. Lime+air
Lime loading=0.05 to 0.4 g $Ca(OH)_2$/g biomass
Time=1 day to 6 wks
Temperature=25 to 80° C.
Air pressure=1 atm
3. Lime+oxygen
Lime loading=0.05 to 0.4 g $Ca(OH)_2$/g biomass
Time=0.5 to 12 h
Temperature=80 to 180° C.
Oxygen pressure=50 to 600 psia After the shock 300 and/or any pretreatment 355 that may be used, the shocked biomass may be optionally blended 356 (such as with solubles 380 and protein), optionally dried 357 (e.g., rotary steam drier, superheated steam), and/or optionally pelleted 358.

FIG. 4 illustrates an animal feed production process similar to FIG. 3, except demonstrating the order of shock 300 and pretreatment 355 may be varied. Moreover, it is within the scope of the disclosure that washing 351 may occur before and/or after shock 300. FIG. 4 shows optional wash 351 with a wash stream 350 may occur before shock 300 and/or pretreatment 355.

Figure 5:
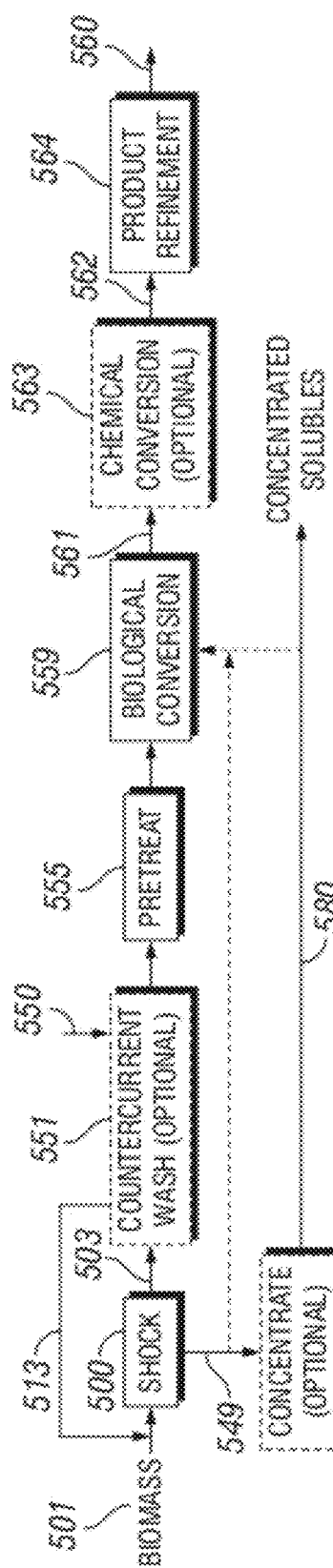
FIGS. 5 and 6 illustrate a block flow diagram for a process for making fuels and chemicals from biomass with shock and pretreat conditions, according to an embodiment of the disclosure.
Figure 6:
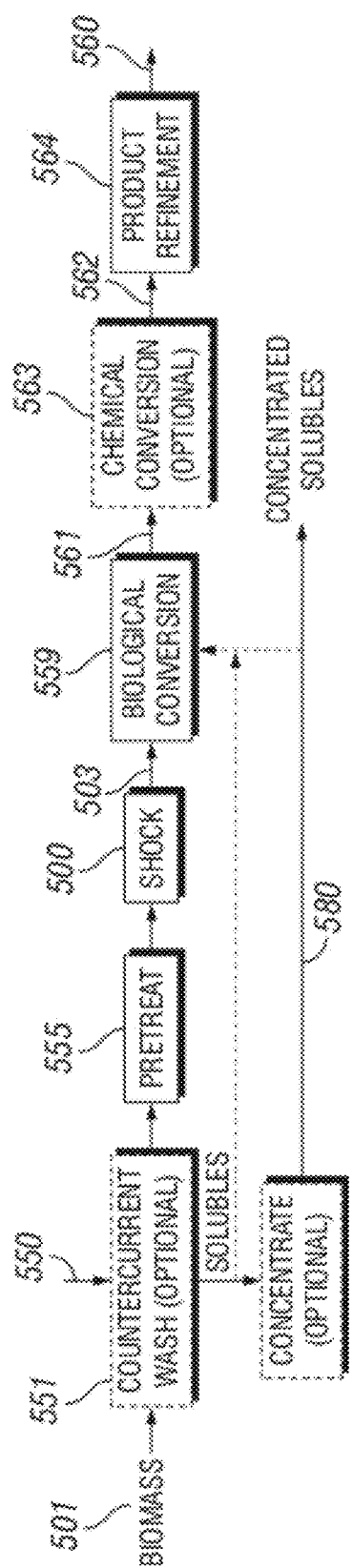

Referring now to FIGS. 5 and 6 together, a biomass conversion process according to embodiments disclosed herein, is shown. FIG. 5 illustrates a process by which biomass 501 may be converted to various non-edibles, such as chemical and fuel products. As shown, shock treatment 500 may occur first, followed by pretreatment 555; however, the order of shock 500 and pretreatment 555 could just as well be reversed. Moreover, the use of pretreatment 555 in conjunction with shock 500 is optional.

The shocked biomass 503 may be biologically converted 559 to products 560. In one embodiment, extracellular enzymes may be added to the shocked biomass, which may produce sugars or sugar-based materials. The sugars may be fermented to an alcohol, such as ethanol, butanol, etc., to an acid, such as succinic acid, lactic acid, etc., or other products.

In other embodiments, microorganisms that produce their own hydrolytic enzymes may be used to convert polysaccharides in the biomass 503 to sugars. The sugars may be fermented to an alcohol, such as ethanol, butanol, etc., to an acid, such as succinic acid, lactic acid, etc., or other products.

In yet other embodiments, mixed cultures of microorganisms that may produce their own hydrolytic enzymes may be used to convert the biomass 503 to form carboxylate salts (e.g., salts of acetate, propionate, butyrate, valerate, caproate, heptanoate), as well as other products, including hydrogen, carbon dioxide, methane, ethanol, and lactic acid.

After the biological conversion 559, an optional chemical step 563 may be used to convert the biological products 561 to products 562, which may be refined to final products 560. For example, carboxylate salts may be concentrated and thermally converted to ketones. The ketones may then be hydrogenated to alcohols, and the alcohols may then be oligomerized to hydrocarbons. After the optional chemical step 563, the products 561 or 562 may be further processed or refined 564, such as with distillation, resulting in final products 560.

FIG. 6 is similar to FIG. 5, except showing the order of shock 500 and pretreatment 555 is not meant to be limited, such that order may be changed. Moreover, it is within the scope of the disclosure that washing 551 may occur before and/or after shock 500. FIGS. 5 and 6 show optional wash 551 with a wash stream 550 may occur before or after shock 500 and/or pretreatment 555.

Figure 7:
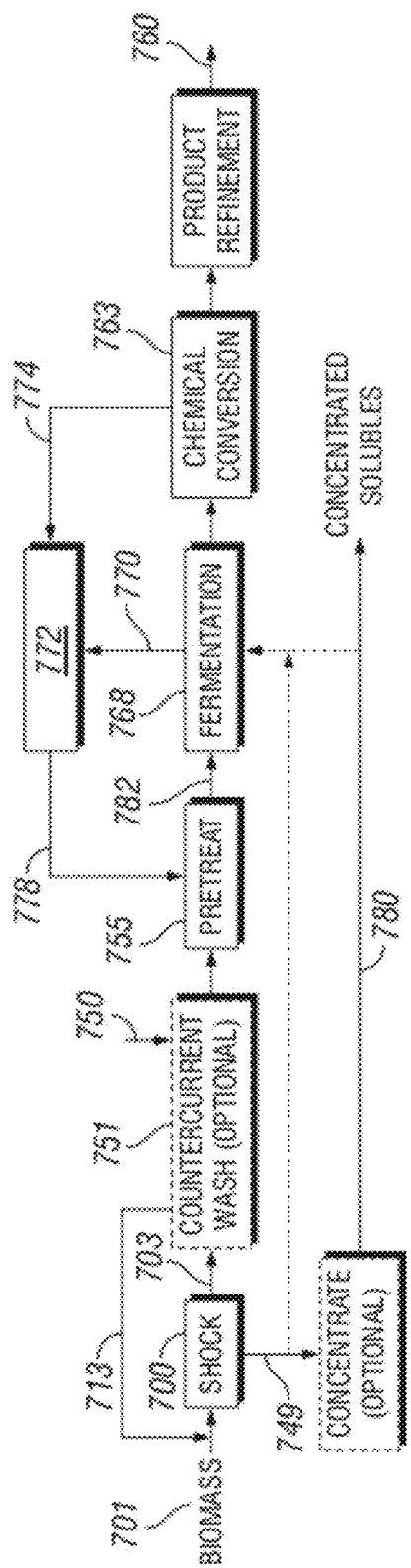
FIGS. 7 and 8 illustrate a block flow diagram for a process for making fuels and chemicals from biomass with shock and pretreat conditions, according to an embodiment of the disclosure.
Figure 8:
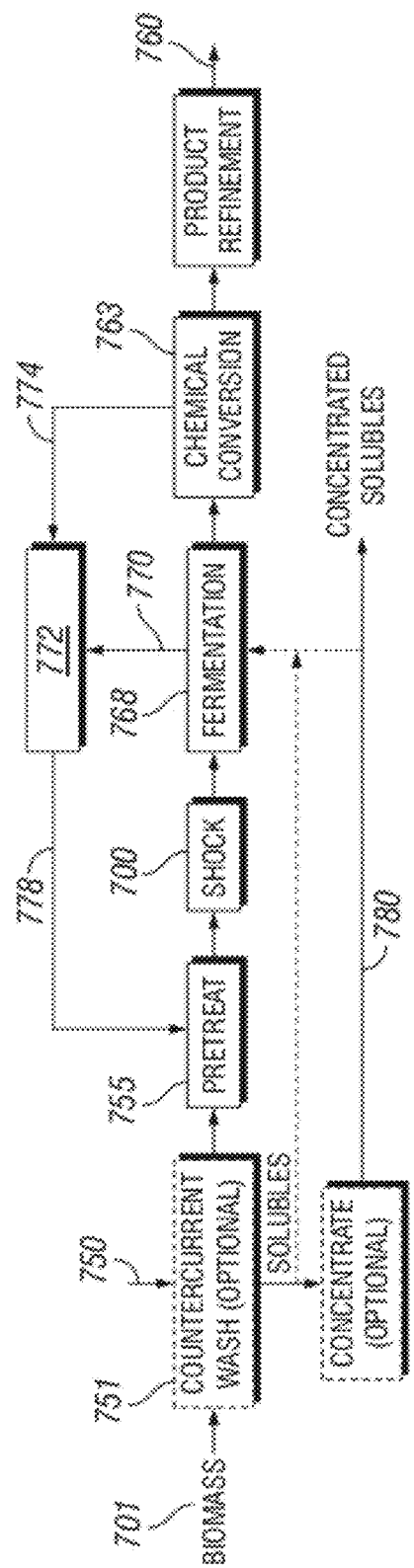

Referring now to FIGS. 7 and 8 together, another biomass conversion process according to embodiments disclosed herein, is shown. FIG. 7 shows a process by which biomass 701 may be converted to products 760, such as chemical and fuel products. In the process, shock treatment 700 may occur first, followed by pretreatment 755 resulting in a pretreated biomass 782. In an embodiment, the pretreatment 755 may be an alkaline pretreatment, whereby an alkaline material is applied to the shocked biomass 703. The resultant pretreated biomass 782 may then be fermented 768. Fermentation 768 may result from using a mixed culture of microorganisms with the pretreated biomass 782 that may produce mixed carboxylate salts, including for example, salts of acetate, propionate, butyrate, valerate, caproate, heptanoate, etc.

Any produced carboxylate salts may be concentrated and/or chemically converted 763. For example, as mentioned above, carboxylate salts may be thermally converted to ketones, alcohols, and hydrocarbons. Alternatively, carboxylic acids may be formed. These acids may be "sprung" from the salts, as has been described in, for example, issued U.S. Pat. Nos. 6,043,392, 6,262,313, and 6,395,926. These patents are hereby incorporated for reference herein in their entirety. Accordingly, any carboxylic acids may be chemically converted to ketones, alcohols, and hydrocarbons.

Materials, such as undigested residue 770 from the fermentation 768, and/or salts 774 from chemical conversion 763 (e.g., calcium carbonate, calcium bicarbonate, magnesium carbonate, magnesium bicarbonate, sodium carbonate, sodium bicarbonate, potassium carbonate, potassium bicarbonate) may be sent to a combustor 772 (or other suitable burner). The combustor 772 may provide high combustion temperatures for any materials burned therein. In an embodiment, alkaline salts (e.g., calcium oxide, magnesium oxide, sodium oxide, potassium oxide) may be inexpensively derived from ash material 778 of the biomass combustor 772.

FIG. 8 is similar to FIG. 7, except showing the order of shock 700 and pretreatment 755 is not meant to be limited, such that order may be varied. Moreover, it is within the scope of the disclosure that washing 751 may occur before and/or after shock 700. FIGS. 7 and 8 show optional wash 751 with a wash stream 750 may occur before or after shock 700 and/or pretreatment 755.

Figure 9:
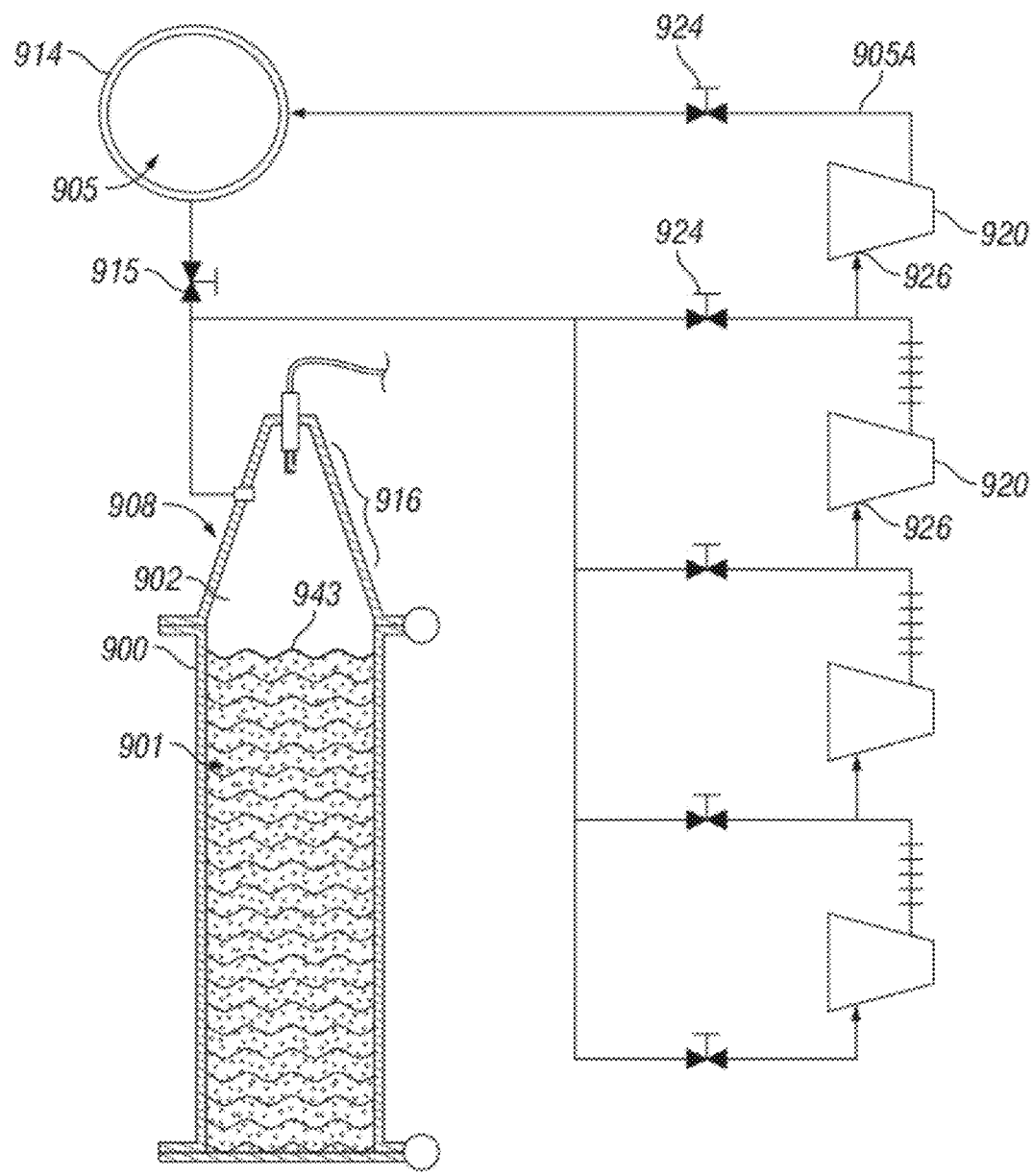
FIG. 9 illustrates a shock tube apparatus, according to an embodiment of the disclosure.

Referring now to FIG. 9, a shock apparatus 900 configured for use with a compressed gas according to embodiments disclosed herein, is shown. FIG. 9 illustrates an embodiment of the shock apparatus in which compressed gas (e.g., air) may be employed. Like any of the apparatuses (e.g., 100, 200, etc.) previously described, the apparatus 900 may be used for shock treatment of biomass.

Operation of the apparatus 900 may be understood with the following description. A slurry of the feed 901 may be loaded into the apparatus 900. In an embodiment, the feed slurry 901 may include biomass, such as lignocellulosic biomass, starchy biomass, tough meat, etc. In another embodiment, the apparatus 900 may be a high-pressure vessel. High-pressure gas 905 from the pressure tank 914 may be instantaneously released into the shock apparatus 900. For example, valve 915 may be manipulated so that gas 905 may flow from the tank 914 into the apparatus 900. Although not shown, a rupture disk (210, FIG. 2) may be used within the shock apparatus 900.

As shown, gas may enter into the apparatus 900 through the upper end 908. Gas may be introduced into the apparatus 900 via a fluid nozzle or inlet (not shown), as would be apparent to one of ordinary skill in the art. In an embodiment, the upper end 908 may be configured with a conical shape 916. The use of a cone or conical shape may efficiently couple the gas from the pressure tank 914 to the top of the liquid slurry 943.

The shock treatment may occur in a manner as previously described, such as with ignition and combustion of gas, or detonation of explosive. After the shock treatment is completed, the gas from the head space 902 may be removed and/or recovered. In an embodiment, the gas may be removed by use of one or more compressors 920. In another embodiment, there may be a series of compressors 920.

With any of the compressors 920, intercooling may be employed between stages. Interstage cooling may reduce the necessary compression energy. After final compression, gas 905A may be fed to the pressure tank 914. Any compressor 920 may have a valve 924 at its respective inlet 926. In an embodiment, the applicable valve 924 may be opened when the interstage pressure is similar the pressure of the shock apparatus 900. When the pressure in the apparatus 900 is high, it may only be necessary to use the top compressor stages. When the pressure in the apparatus 900 is low, it may be necessary to use the lower stage compressors. After the gas is recovered from the apparatus, the shocked slurry may be removed from the shock apparatus 900 so the cycle can be repeated.

Figure 10:
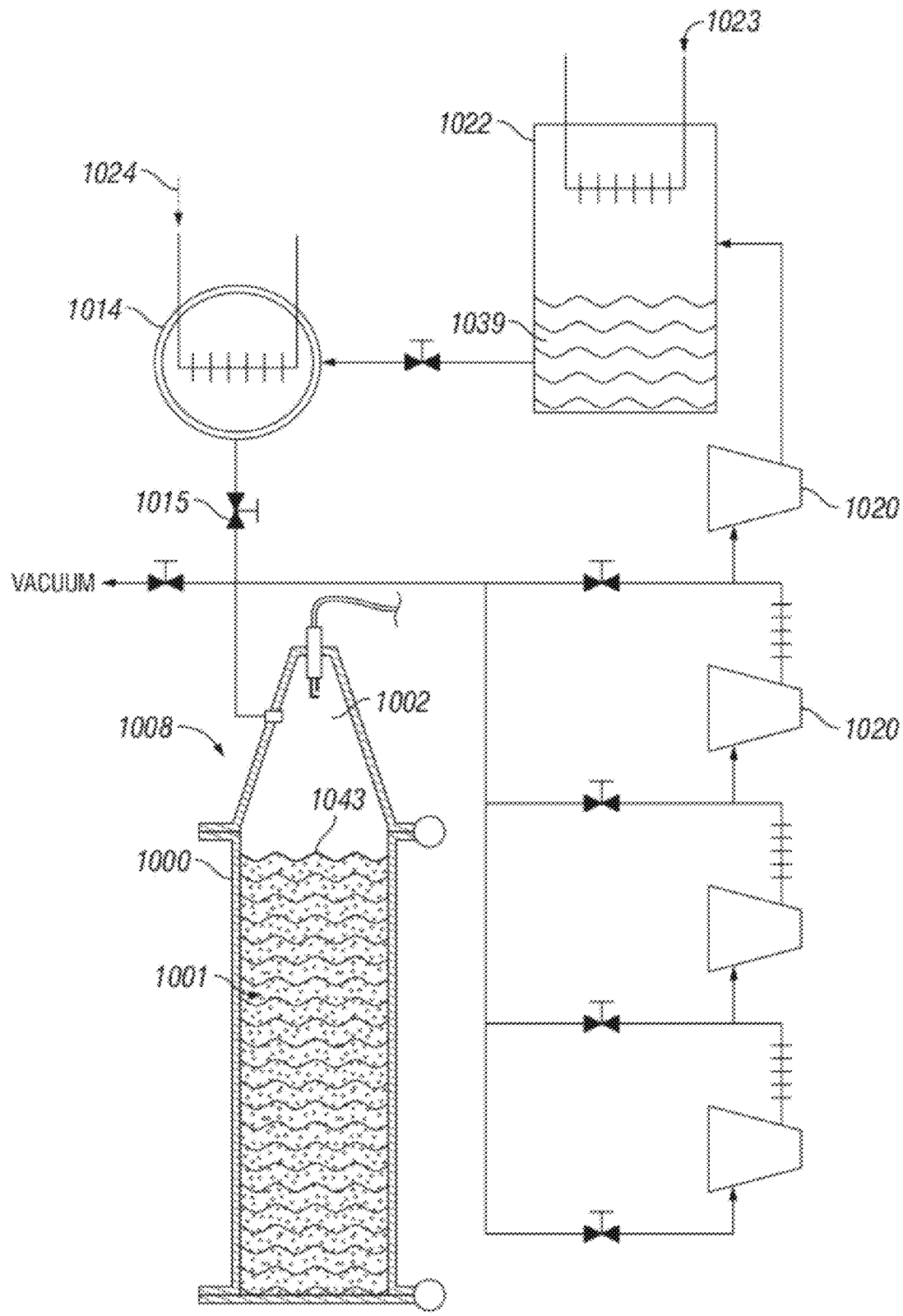
FIG. 10 illustrates a shock tube apparatus with high-pressure liquid condensed at cooling water temperatures, according to an embodiment of the disclosure.
Figure 11:
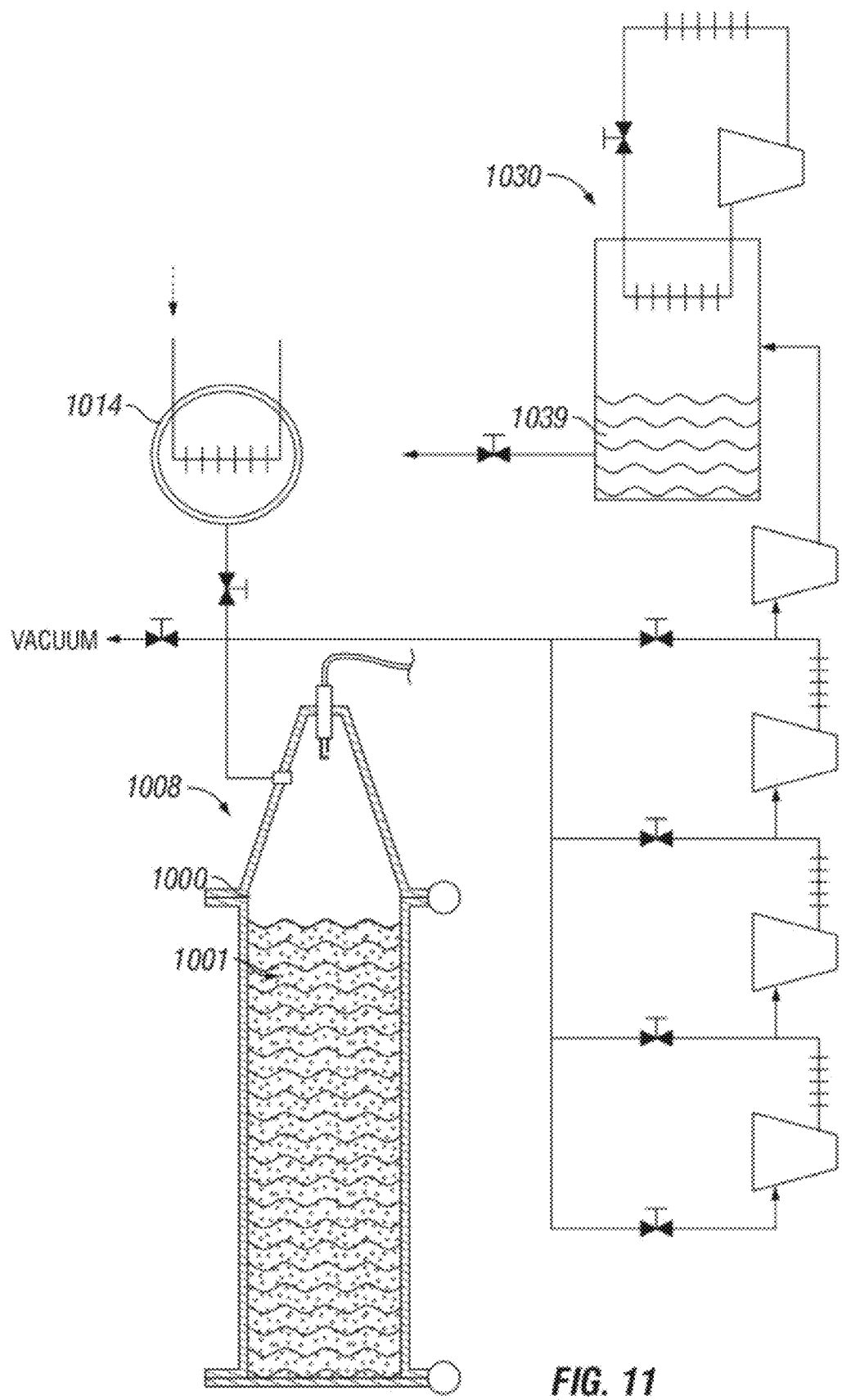
FIG. 11 illustrates a shock tube apparatus with high-pressure liquid condensed at chiller temperatures, according to an embodiment of the disclosure.

Referring now to FIGS. 10 and 11 together, a shock apparatus 1000 configured for use with a condensable liquid according to embodiments disclosed herein, is shown. FIG. 10 illustrates an embodiment of the shock apparatus in which a condensable liquid 1039 (e.g., carbon dioxide) may be introduced into the pressure tank 1014. Like any of the apparatuses described herein, the apparatus 1000 may be used for shock treatment of a biomass slurry 1001.

Operation of the apparatus 1000 may be understood by way of example with the following description. The slurry of biomass feed 1001 (e.g., lignocellulosic biomass, starchy biomass, tough meat) may be loaded into the shock apparatus 1000. Gas may enter a condensation vessel 1022, where a cooling medium 1023, such as cooling water, may be circulated therethrough (e.g., tubes, coils, etc.) in order to condense at least a portion of the gas. High-pressure liquid 1039 from the vessel 1022 may be introduced or otherwise transferred, such as with a pump (not shown), into the pressure tank 1014. In an embodiment, liquid in the pressure tank 1014 may be heated by way of heating medium 1024, such that the temperature and pressure of the liquid 1005 or tank 1014 may be increased. Heat may be transferred from the medium 1024 into the tank 1014, such as with tubes or coils. The heat source 1024 may be, for example, steam, molten salt, hot gas, electricity, or other suitable heating medium or device as would be apparent to one of ordinary skill in the art.

Non-condensable gases may be evacuated from the head space 1002 of the shock apparatus 1000, such as by pulling a vacuum. As exemplified by the depiction FIG. 10, high-pressure fluid from the pressure tank 1014 may be introduced to the shock apparatus 1000 by rapidly opening the valve 1015. In embodiments, a rupture disk (not shown) may be employed in the apparatus 1000.

As shown, high-pressure fluid may enter the apparatus 1000 through the upper end 1008. In an embodiment, the upper end 1008 may be configured with a conical shape 1016. The use of a cone or conical shape may efficiently couple the fluid 1005 from the pressure tank 1014 to the top of the liquid slurry 1043. The shock treatment may occur in a manner as previously described, such as with ignition and combustion of the fluid, or detonation of explosive. After the shock treatment is completed, any gas in the head space 1002 may be removed and/or recovered. In an embodiment, the gas may be removed using one or more compressors 1020. In another embodiment, there may be a series of compressors 1020.

FIG. 11 shows an embodiment of the shock apparatus 1000. This embodiment is comparable to the embodiment shown by FIG. 10, and also may include a chiller system 1030 operatively associated therewith. The chiller system 1030 may be used to condense the liquid 1039 at a temperature lower than may be achieved with the aforementioned cooling medium.

Figure 12:
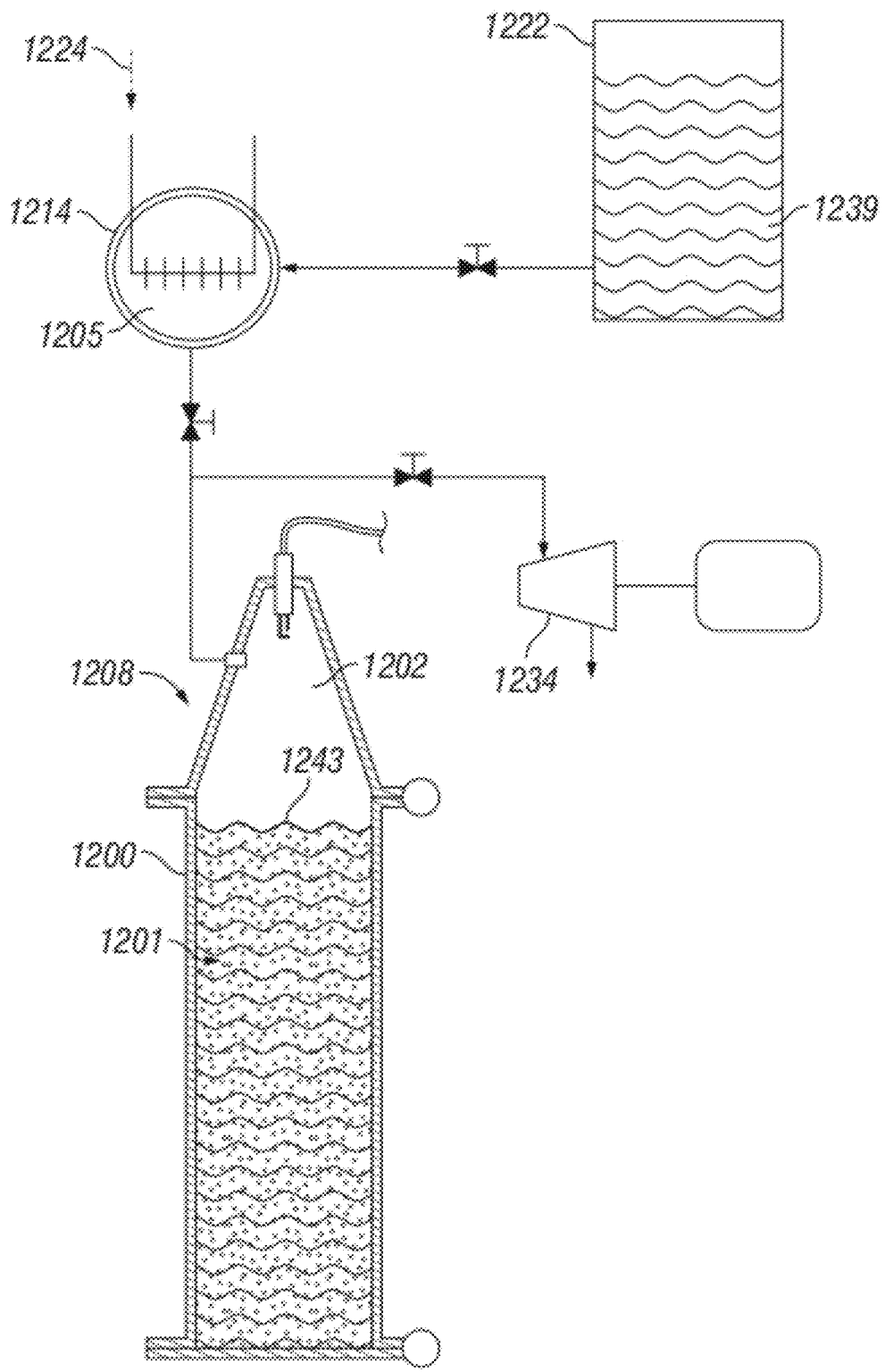
FIG. 12 illustrates a shock tube apparatus with high-pressure liquid that is vented after the shock, according to an embodiment of the disclosure.
Figure 13:
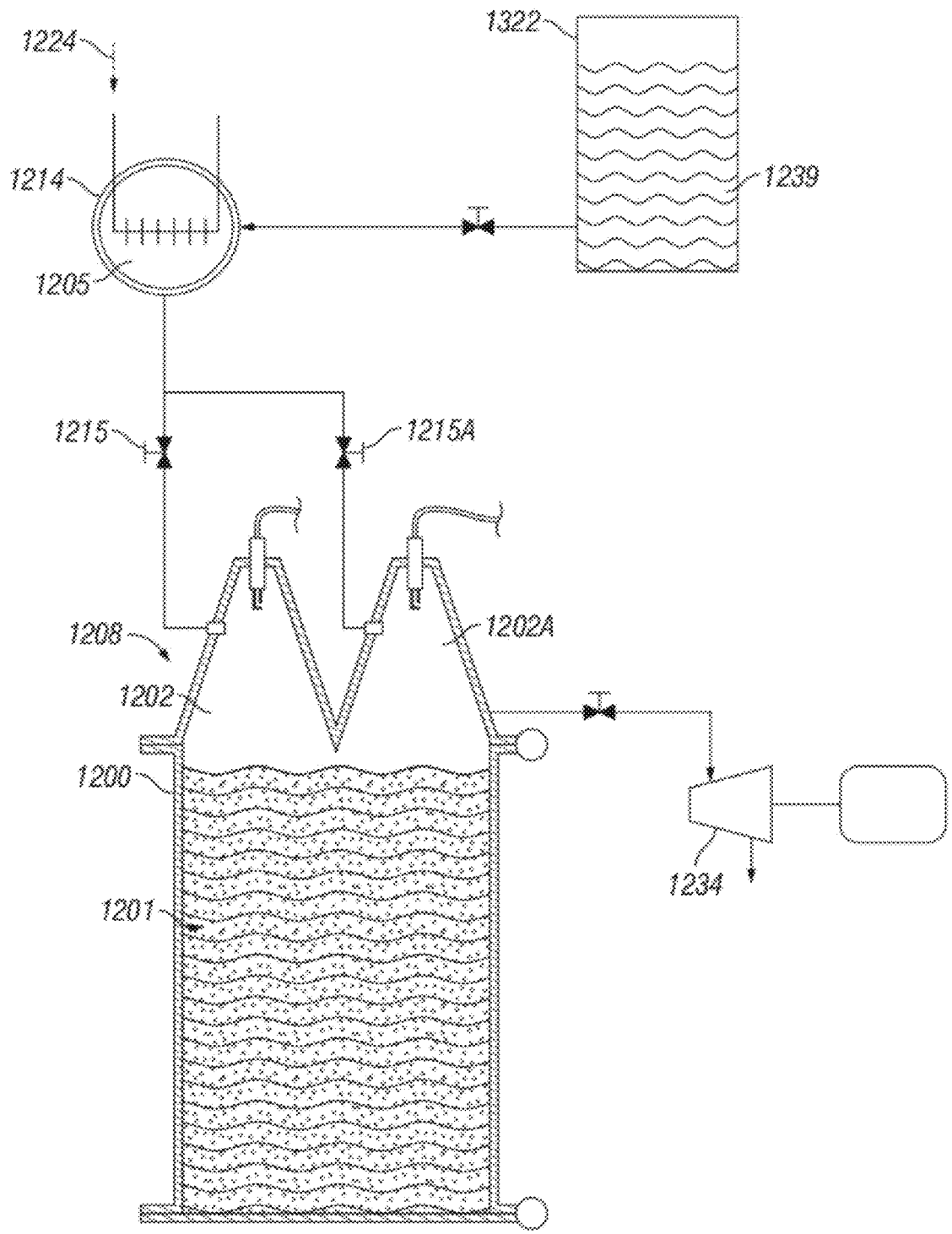
FIG. 13 illustrates a shock tube apparatus with multiple cones servicing the head space, according to an embodiment of the disclosure.

Referring now to FIGS. 12 and 13 together, another shock apparatus 1200 configured for use with a condensable liquid according to embodiments disclosed herein, is shown. FIG. 12 illustrates an embodiment of the shock apparatus 1200 in which a condensable liquid 1239 (e.g., carbon dioxide) may be introduced into the pressure tank 1214. Liquid 1239 from source vessel 1222 may be introduced or otherwise transferred, such as with a pump (not shown), into pressure tank 1214.

Operation of the apparatus 1200 may be understood by way of example with the following description. A slurry of biomass feed 1201 (e.g., lignocellulosic biomass, starchy biomass, tough meat) may be loaded into the shock apparatus 1200. A source vessel 1222 of high-pressure liquid 1239 may be fluidly connected with a pressure tank 1214. As such, high-pressure liquid, such as liquid carbon dioxide, may be introduced to the pressure tank 1214. In an embodiment, liquid 1205 in the pressure tank 1214 may be heated with a heat medium 1224, whereby the temperature and pressure of the tank 1214 and/or liquid 1205 may be increased. Heat may be transferred from the medium 1224 into the tank 1214, such as with tubes or coils. The heat medium 1224 may be, for example, steam, molten salt, hot gas, electricity, or other suitable heating medium or device as would be apparent to one of ordinary skill in the art.

High-pressure liquid 1205 from the pressure tank 1214 may be introduced to the shock apparatus 1200 through upper end 1208 by way of opening the valve 1215. [Note: the valve is not labeled in the figure.] In an embodiment, a rupture disk (not shown) may be employed. In another embodiment, the upper end 1208 may be configured with a conical shape. The use of a cone or conical shape may efficiently couple liquid 1205 from the pressure tank 1214 to the top of the liquid slurry 1243 in the apparatus 1200. The shock treatment may occur in a manner as previously described, such as with ignition and combustion of the gas, or detonation of explosive. After the shock treatment is completed, any gas or vapor in the head space 1202 may be removed (e.g., venting) and/or recovered. In an embodiment, the gas may be removed using one or more compressors. In another embodiment, gas may be vented through an expander 1234, such that energy may be recovered from the gas. After gas is removed, the shocked biomass may be removed from the shock apparatus 1200, and any aspects of the cycle of operation may be repeated.

FIG. 13 illustrates the shock apparatus 1200 may be configured with multiple cones to services the head spaces 1202, 1202A. Multiple cone features may reduce the head space volume, which as a result may reduce the amount of high-pressure fluid needed, thus saving operating expenses. Although FIG. 13 is illustrated as a variant of FIG. 12, it is within the scope of the disclosures that multiple cones may be used with any method or apparatus described herein.

Referring now to FIGS. 14A-14D, a shock tube apparatus 1400 configured for biomass loading and processing, according to embodiments disclosed herein, is shown. The shock apparatus of the disclosure, and any components or subcomponents thereof, may be made from any number of metals, alloys, compositions, etc., as would be known to one of ordinary skill in the art. Connections between components and subcomponents may be by conventional connections as also known to one of skill, such as, for example, threaded, welded, sealed, flanged, etc. A specific example of apparatus 1400 is described as follows.

In one embodiment, the shock tube apparatus 1400 may be about 66-in high (including frame), and may have an approximate diameter of about 11-in at its widest point. Varying amounts of biomass slurry (e.g., 101, FIG. 1) may be loaded into a lower portion 1452 of the apparatus 1400. In an embodiment, the lower portion 1452 may be steel pipe, with about 20-in length and about 4.5-in outer diameter (3.8-in inner diameter). The lower portion 1452 may be configured with one or more flanges 1499. For example, flange 1499 may be a 1-in-thick by 9.5-in-diameter circular steel flange welded onto each end 1408, 1409 of the lower portion 1452. Each open end of the flanges 1499 may be sealed with mating end cap flanges 1445, 1446. End flanges 1445, 1446 may likewise be 1-in-thick by 9.5-in-diameter circular metal flanges. There may be a gasket 1498 disposed therebetween, with the flanges held on by one or more bolts 1497 (and nuts 1496) at each end.

Figure 14C:
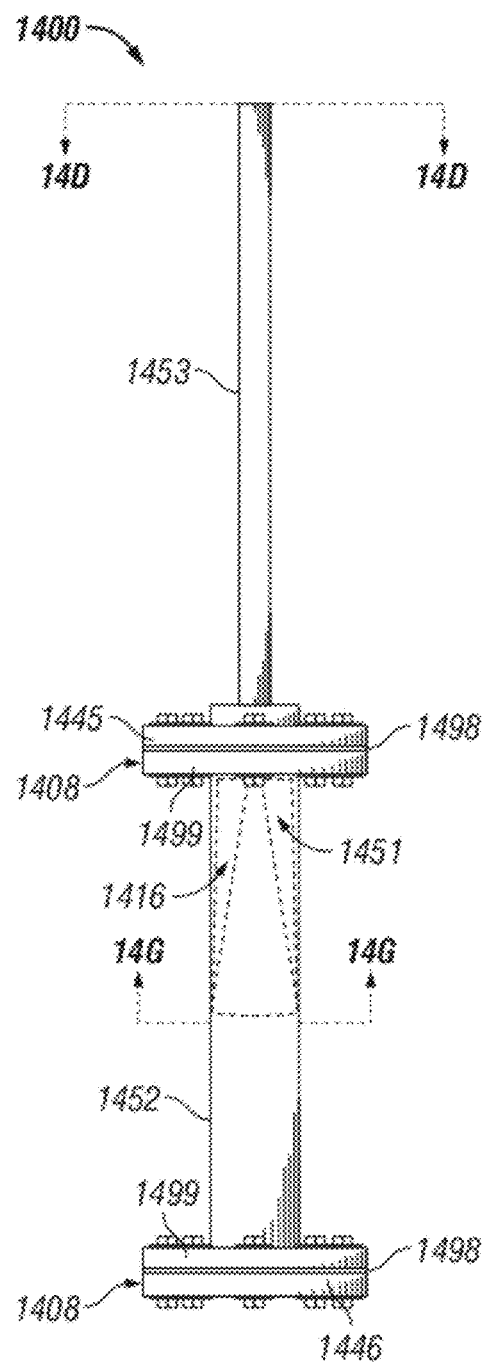
Figure 14D:
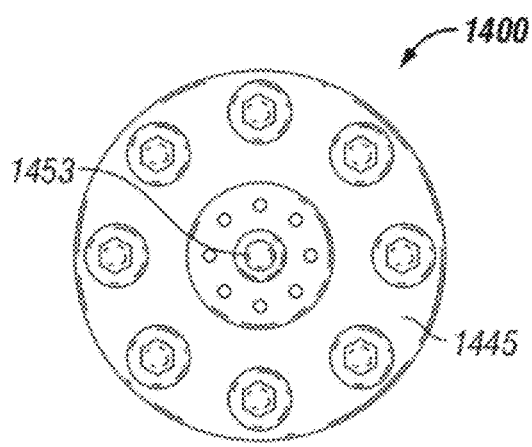
Figure 14E:
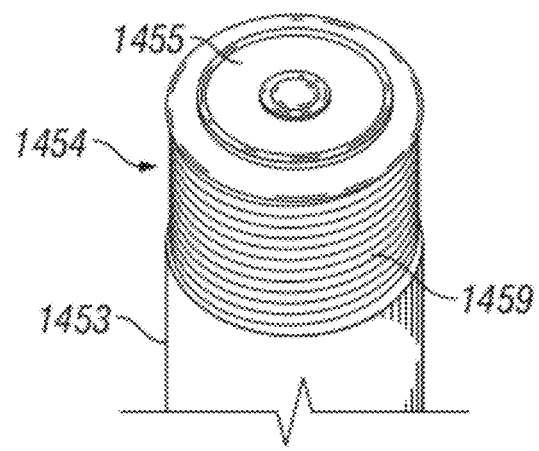
FIGS. 14E-14F illustrate a shotgun shell and firing mechanism usable with a shock apparatus, according to an embodiment of the disclosure.
Figure 14F:
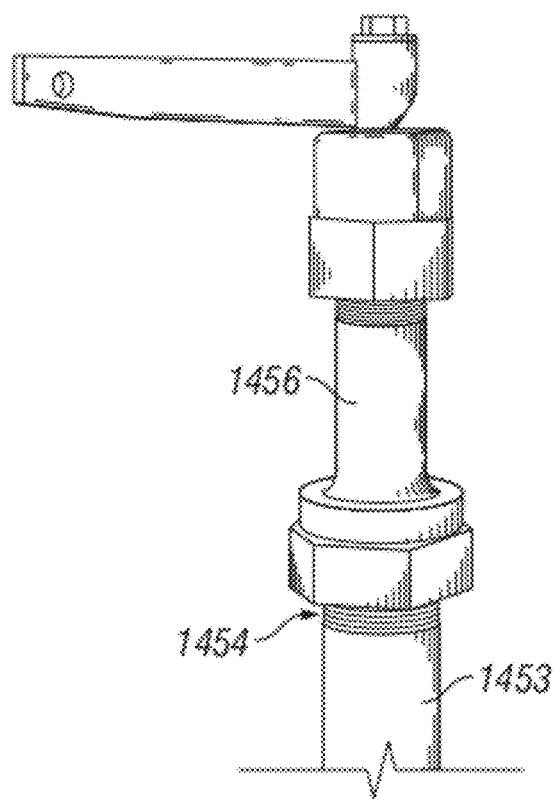
Figure 14G:
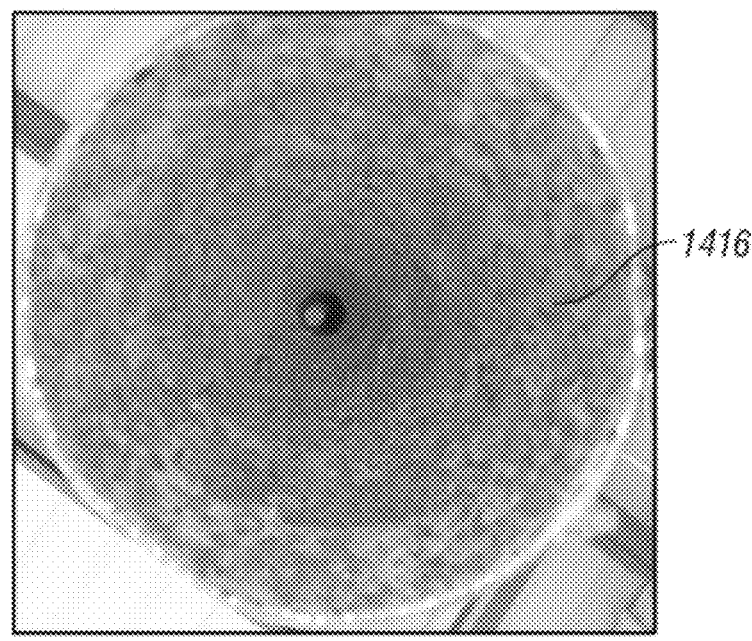
FIG. 14G illustrates a conical surface of a shock apparatus, according to an embodiment of the disclosure.

The upper portion 1451 may include the flange 1445 welded thereto. The upper portion 1451 may include an inner conical shape 1416. In an embodiment, the upper portion 1451 is an elongated steel cylinder, where the cylinder is bored out, such that the cone shape 1416 is formed therein, as illustrated by FIG. 14G. As an example, the size of the cone may include the largest inner diameter at the bottom portion of the cone 1416 and the smallest inner diameter at the top of the cone 1416. This shape may help focus shock waves onto and against the biomass.

A barrel 1453 may be connected to top of the upper portion 1451, such as be welding or the like. In an embodiment, the barrel 1453 may be 28-in long, with 1.5-in O.D. The barrel 1453 may be configured for an explosive device or material to fit therein. Referring briefly to FIGS. 14E and 14G together, these figures illustrate the barrel 1453 may be configured to receive, for example, a shotgun shell 1455 inside the open top end 1454 of the barrel 1453. Threads 1459 on the top end may provide the ability to have a firing mechanism 1456 be securely fastened to the barrel 1453. In an embodiment, the firing mechanism 1456 may be, for example, a spring-loaded firing pin, which may strike the top of the shotgun shell 1455 causing a blast to discharge therefrom. When the shotgun shell 1455 detonates, the result is a shock wave through the biomass that may disrupt the biomass physical structure and enhance enzymatic digestibility.

Referring now to FIGS. 15A-15F together, a shock apparatus operational with a fill, shock, and dump cycle, according to embodiments disclosed herein, is shown. Apparatus 1500 may be used with other processes and methods disclosed herein, and/or may include features or elements of other apparatuses of the present disclosure previously described, as would be apparent to one of skill in the art. In an embodiment, apparatus 1500 may be a cylindrical main body 1510 with two end caps 1545, 1546 mateable on each end 1508, 1509, respectively, of the main body 1510. Although shown as cylindrical or tubular in nature, the main body 1510 may be other shapes, such as oval, conical, square, modular, etc.

The shock apparatus 1500 may be configured for rapid transfer of a biomass 1501 to and therefrom. The apparatus 1500 may include the main body 1510 having a chamber or internal compartment 1511. The chamber 1511 may be configured for biomass 1501 transferred therein to be subjected to a shock (e.g., shock event). In an embodiment, the biomass 1501 may be lignin-based or grain-based.

The apparatus 1500 may include the first end cap or cover 1545 movably associated or pivotably connected with the first end 1508. Similarly, the apparatus may include the second end cap or cover 1546 movably associated or pivotably connected with the second end 1509. The apparatus 1500 may include a frame structure 1558, which may be used for holding the main body 1510 in a predetermined orientation (e.g., up, down, sideways, etc.). The predetermined orientation may be with respect to a horizontal, such as the ground. In an embodiment, a long axis (not shown) of the main body 1510 may be substantially vertical (i.e., perpendicular) with respect to an earthen surface.

There may be a first actuator 1570 coupled with the frame 1558, the first actuator configured for opening and closing the first end cap 1545. The actuator 1570 may be coupled with the frame in conventional fashion, such as nut and bolt or welding. The apparatus 1500 may also include a first clamp 1560 coupled with the frame 1558, the first clamp 1560 being operable to hold and maintain the first end cap 1545 in a sealingly engaged position with the first end 1508. The first clamp 1560 may be coupled with the frame 1558 via connection with a corresponding piston-ram mechanism 1580. That is, the first clamp 1560 may be attached to a sliding piston 1561, the piston 1561 being operable to extend (1585) and retract (1585A) via operation of the mechanism 1562.

In embodiments, the apparatus 1500 may further include a second actuator 1572 coupled with the frame 1558, whereby the second actuator 1572 may be configured for opening and closing the second end cap 1546. The second actuator 1572 may be coupled with the frame in conventional fashion, such as nut and bolt or welding, such as at coupling point 1543 of the frame 1558. The apparatus 1500 may also include a second clamp 1586 coupled with the frame 1558, the second clamp 1586 being operable to hold and maintain the second end cap 1546 in a sealingly engaged position with the second end 1509. The second clamp 1586 may be coupled with the frame 1558 via connection with a corresponding piston-ram mechanism 1564. That is, the second clamp 1586 may be attached to a sliding piston 1565, the piston 1565 being operable to extend and retract via operation of the mechanism 1564.

It should be appreciated that the apparatus 1500 may include one or more additional first clamps or second clamps, the additional clamps also being operable to hold the first or second end caps in closed, sealingly engaged positions with the first and second ends, respectively. Each of the clamps may be movable by way of connection with a sliding piston and a ram mechanism, as would be apparent to one of skill in the art. In an embodiment, at least one of the movable pistons and clamps is pneumatically, hydraulically, or electrically actuated. Although not necessary, all of the clamps and associated mechanisms may be identical. Although not shown, each of the ram/piston/clam mechanisms and/or the actuators may be complimented with circuitry, fittings, hydraulics, utilities, etc. as may be necessary to provide the device(s) with operability, as would be apparent to one of skill in the art.

The upper and lower end caps 1545, 1546 may be associated or connected with the apparatus 1500. In an embodiment, end caps 1545 and/or 1546 may be flanges connectable to the apparatus 1500 via a flange connection (not shown). In other embodiments, end caps 1545 and/or 1546 may be associated with the ends 1508, 1509, respectively, in a movable or rotatable fashion, such as with a hinge, which may operate in conjunction with an actuatable pivot mechanism 1574.

A portion 1539 of the pivot mechanism 1574 may be connected, or otherwise affixed to, the main body 1510 at surface point 1544. Affixing part of the mechanism 1574 provides the ability to have movement (or moment) around pivot 1575. The ability to open and close the apparatus 1500 provides for a biomass or biomass slurry 1501/1503 to be rapidly added and removed therefrom. In some aspects, the upper end cap 1545 may include a conical shape portion 1516 attached therewith, whereas in other aspects the end caps 1545, 1546 may be flat. In an embodiment, the biomass slurry 1501 may be an aqueous slurry.

Figure 15A:
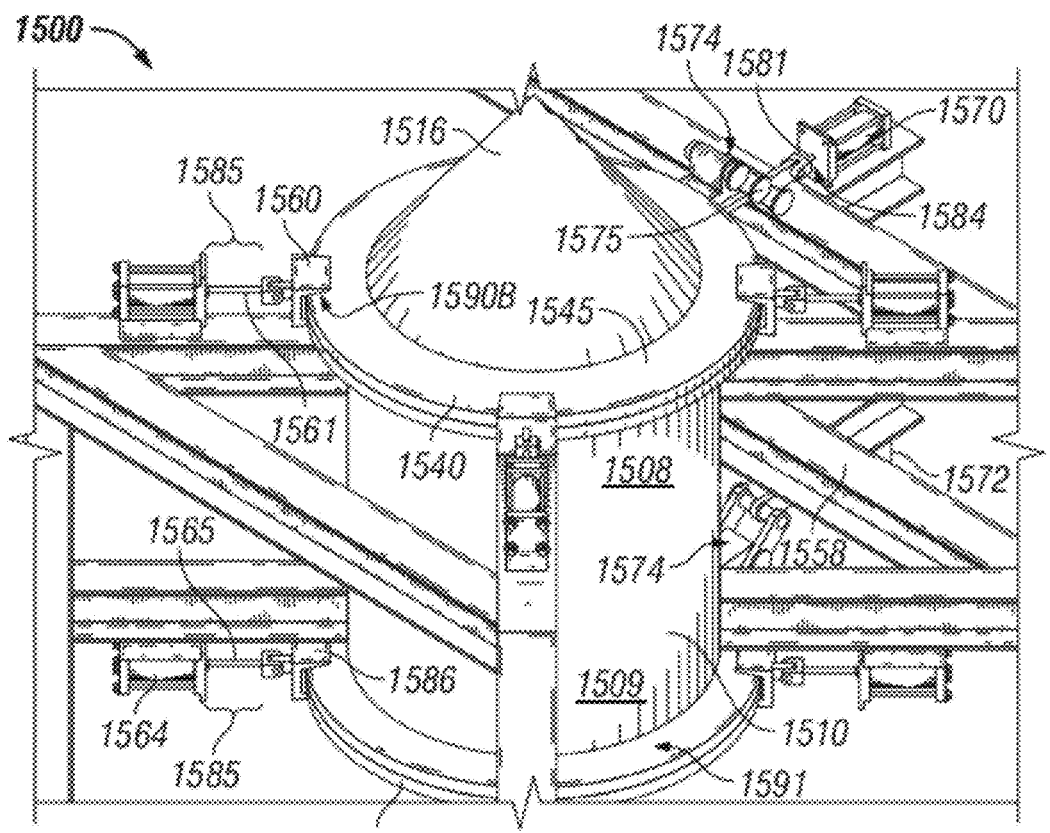
FIGS. 15A-15F illustrate a shock apparatus operable with a fill, shock, and dump cycle, according to an embodiment of the disclosure.
Figure 15B:
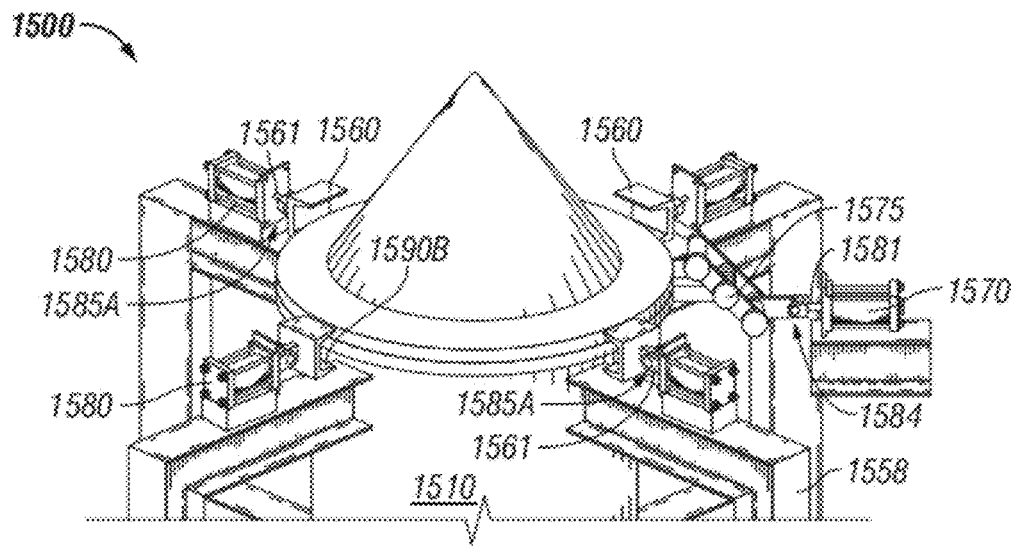
Figure 15C:
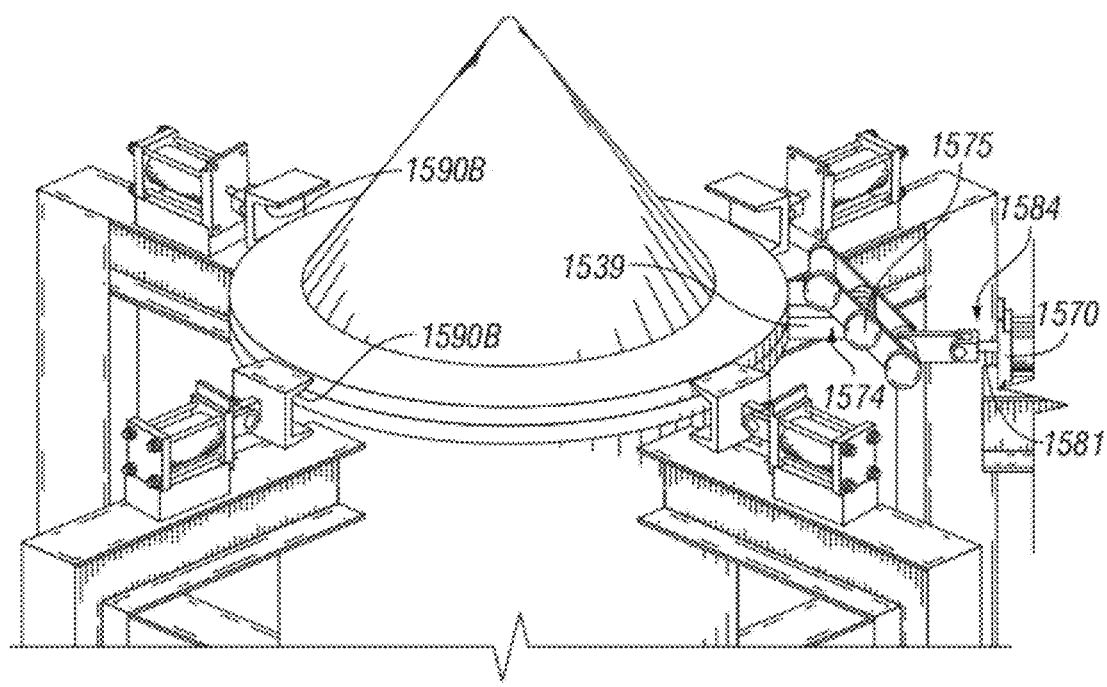
Figure 15D:
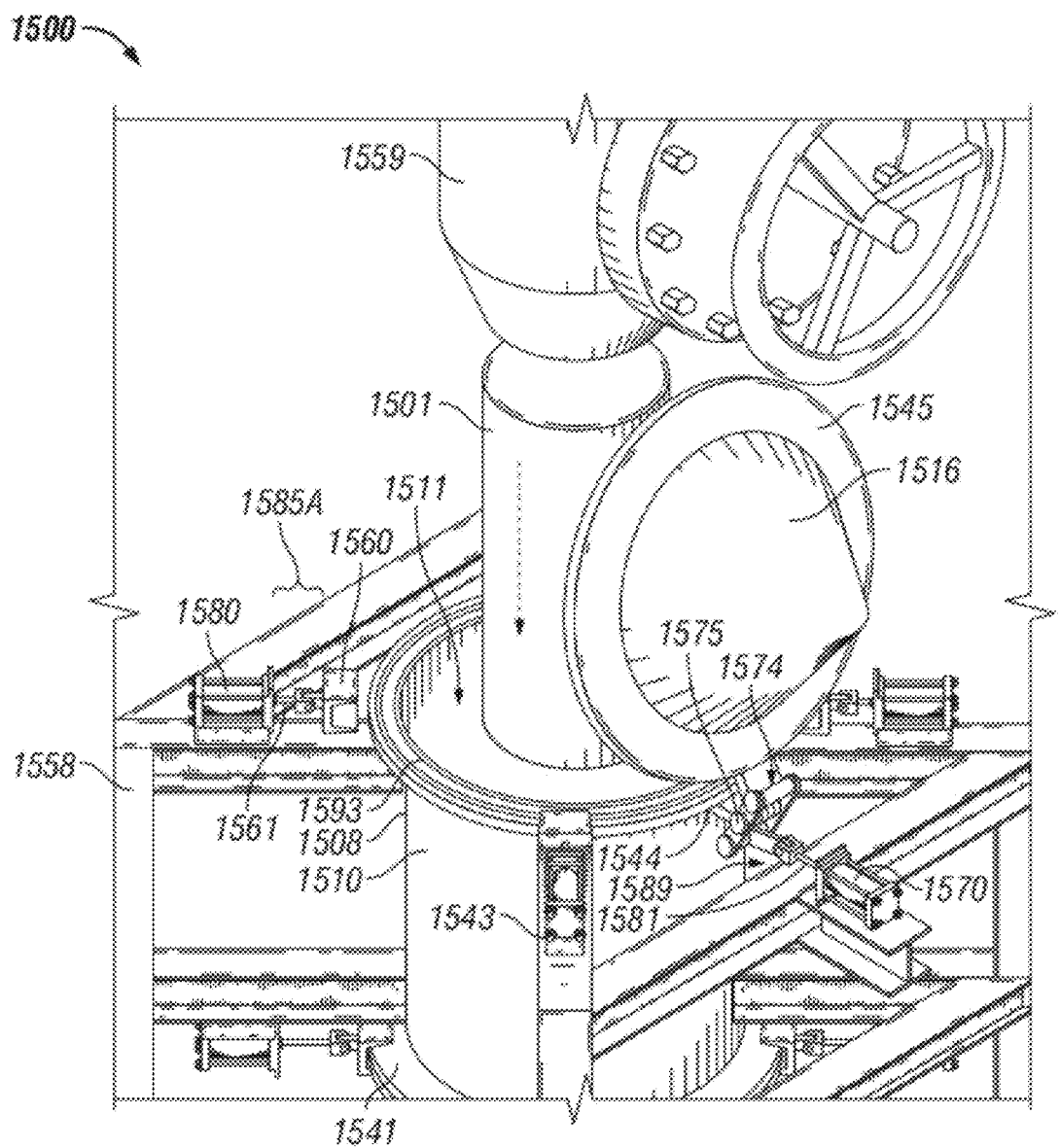

FIGS. 15A-15D illustrate a fill and shock cycle. Initially, the end cap 1545 may be in a closed position (FIG. 15A), and held in place by one or more of the clamps 1560. The clamp(s) 1560 may be connected to the respective movable piston mechanism 1580. The clamps 1560 may be retracted from an extended position 1585 (FIG. 15A) to a refracted position 1585A (FIG. 15B-D). When the clamps 1560 are retracted far enough way from the end cap, the end cap 1545 may be opened, as shown in FIG. 15D. As part of this sequence, the actuator 1570 may be activated and as a result a rotation or pivot moment induced into the pivot mechanism 1574. In activating the pivot mechanism 1574, the piston 1581 of the first actuator 1570 extends outward from a first position 1584 (FIG. 15A) to a second position 1589 (FIG. 15D), whereby extension (or vice versa) causes the mechanism 1574 to experience movement around pivot point 1575. The movement around the pivot point 1575 results in the first cap 1545 moving upward from the first end 1508 to an opened position, as shown in FIG. 15D. Closing of the end cap 1545 occurs from reverse operation of the actuator 1570.

FIG. 15D also shows the biomass slurry 1501 may be introduced into the apparatus 1500, such as from an overhead bin or feeding tube 1559 (also, feeder, hopper, etc.). The biomass may be transferred to the apparatus 1500 through the first end 1508 of the main body 1510. After biomass slurry 1501 is added to the shock apparatus 1500, the end caps 1545 and/or 1546 may be sealingly closed, thus creating an internal environment within the apparatus 1500 that may be isolated from external surroundings. The biomass 1501 may be subjected to a shock event. In an embodiment, the shock event may include a time lapse of less than 1 second, and a pressure increase of at least 100 psi.

There may be one or more seals or gaskets 1593 disposed between the end 1508 and the end cap 1545, and there may be one or more seals or gaskets 1593 disposed between the second end 1509 and the end cap 1546. The seals or gaskets may be suitable for helping form the sealing engagement between surfaces, as would be apparent to one of sill in the art.

The shock event may result from ignition of a gaseous mixture fed into the chamber 1511. Internal of the apparatus 1500, a head or vapor space above any liquid level in the chamber 1511 may be filled with gas (not shown). Gas may be introduced into the apparatus 1500 via a fluid nozzle or inlet (not shown), as would be apparent to one of ordinary skill in the art. In an embodiment, the gas may be a flammable gas (e.g., methane, hydrogen). In addition, the apparatus must also contain a suitable oxidant (e.g., air, oxygen). The gas may be a mixture of flammable gas combined with an oxidant, such as oxygen, air, etc. In operation, the gas mixture may be ignited, such as with an igniter device, as previously explained and as apparent to one of skill in the art for igniting the gas mixture.

Figure 15E:
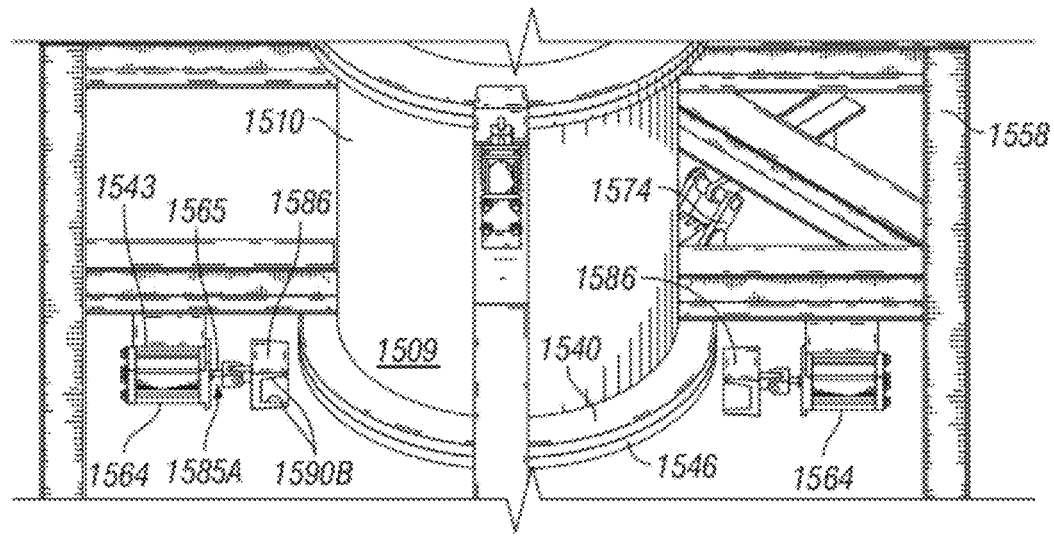
Figure 15F:
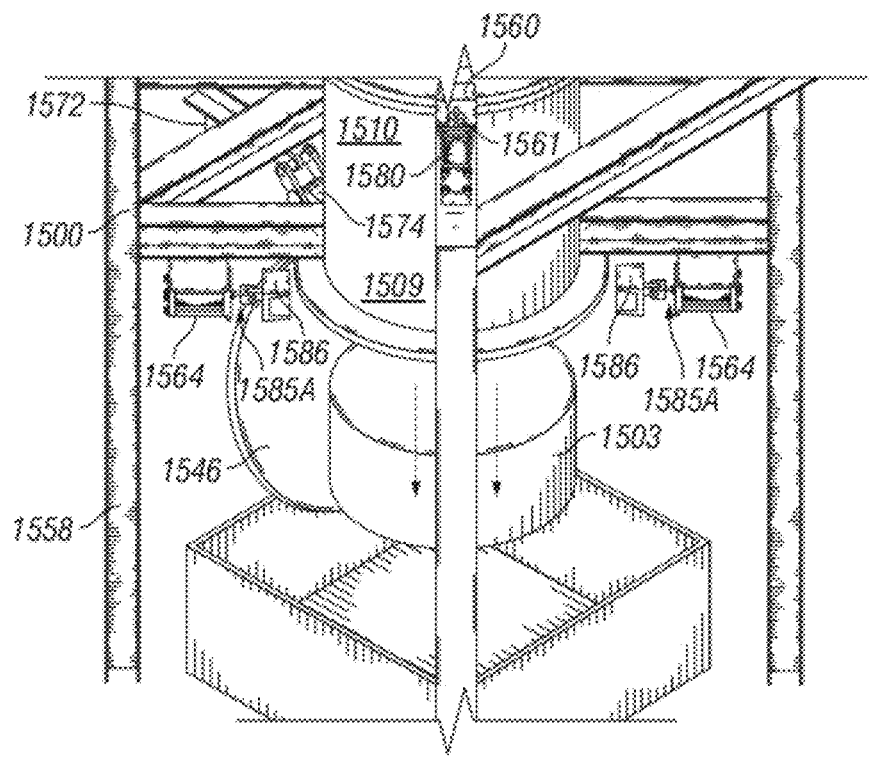

FIGS. 15E-15F illustrate aspects of the dump cycle. After the shock treatment, the shocked biomass 1503 may be removed or emptied from the apparatus 1500, as shown in FIG. 15F, at which point any aspect of the entire cycle may be repeated as desired. In an embodiment, the shocked biomass 1503 may be transferred from the apparatus 1500 through the second end 1509.

Initially, the end cap 1546 may be in a closed position (FIG. 15E), and held in place by one or more of the clamps 1586. The clamp(s) 1586 may be connected to the respective movable piston mechanism 1564. The clamps 1586 may be refracted from an extended position 1585 (FIG. 15A) to a retracted position 1585A (FIG. 15E-F). When the clamps 1586 are retracted far enough way from the end cap, the end cap 1546 may be opened, as shown in FIG. 15F. As part of this sequence, the actuator 1572 may be activated and as a result a rotation or pivot moment induced into the pivot mechanism 1574. In activating the pivot mechanism 1574, the piston 1538 of the first actuator 1572 extends outward to a second position shown by FIG. 15F, whereby extension (or vice versa) causes the mechanism 1574 to experience movement around pivot point 1575. The movement around the pivot point 1575 results in the second end cap 1546 moving away from the second end 1509 to an opened position, as shown in FIG. 15F. Closing of the second end cap 1546 occurs from reverse operation of the actuator 1572.

Figure 15G:
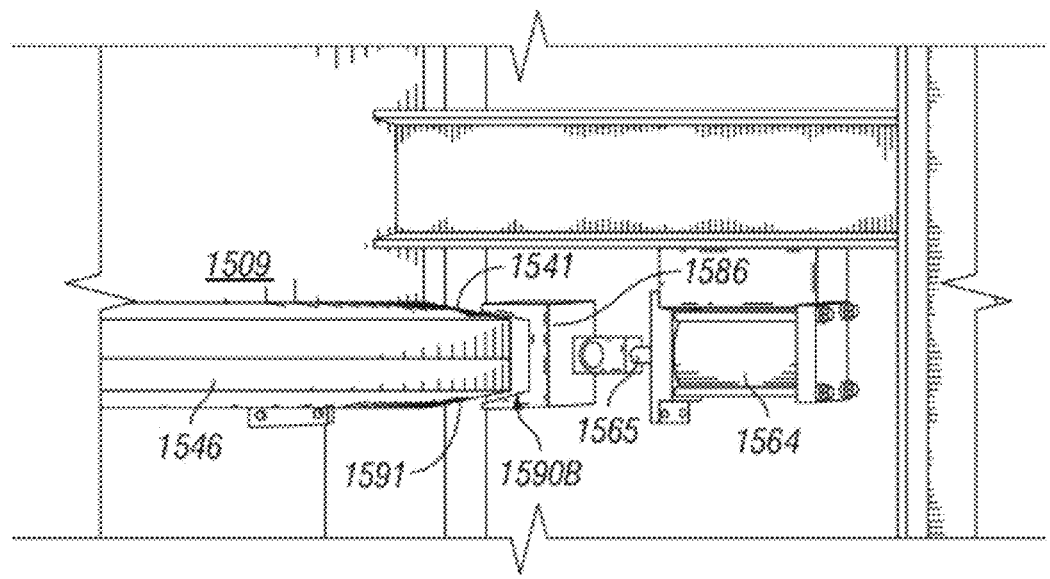
FIGS. 15G-15H illustrate a shock apparatus configured with one or more sloped surfaces, according to an embodiment of the disclosure.
Figure 15H:
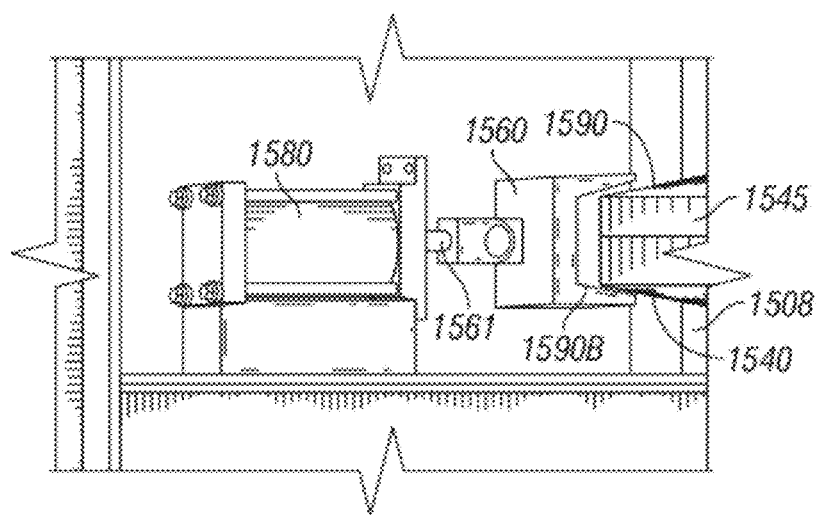

Referring to FIGS. 15G-15H together, a shock apparatus configured with one or more sloped surfaces, according to embodiments disclosed herein, is shown. FIGS. 15G-15H, illustrate either of the end caps 1545, 1546 may be configured with a sloped surface. Thus, the first end cap 1545 may be configured with the first sloped surface 1590. Likewise, the second end cap 1546 may be configured with a second sloped surface 1591. The corresponding surfaces on the ends 1508, 1509 may also be configured with sloped surfaces 1540, 1541, respectively. Comparably, any of the clamps 1560, 1586 may have a corresponding sloped surface 1590B. For example, clamp 1560 may have one or more sloped surfaces 1590B. FIG. 15G illustrates clamp 1586 with two sloped surfaces 1590B.

In some embodiments, engagement between the first clamp 1560, the first sloped surface 1590, and the main body (i.e., first end 1508) may result in compression therebetween as a result of the piston being moved to the extended position (1585, FIG. 1). In other embodiments engagement between the second clamp 1586, the second sloped surface 1591, and the main body (i.e., second end 1509) may result in compression therebetween as a result of the piston 1565 being moved to the extended position (1585, FIG. 1).

Example Shock Tube Procedure

Before shock treatment, biomass samples were prepared by air drying the biomass to a moisture content of approximately 5%. The biomass was ground, if desired, to a consistent particle size, and samples were weighed out in 100-g batches and stored in labeled Zip-Loc freezer bags. For frozen samples, the desired amount of water (typically 200 mL) was added to the biomass in the freezer bag, mixed thoroughly, and the sample was stored in the freezer. For non-frozen samples, the 200 mL of water was added and mixed the day of the shock treatment, before being delivered to the shock tube site.

Supplies gathered and transported to the shock tube site included gloves, safety glasses, paper towels, several 4-L plastic buckets, a stainless steel sieve (80 mesh), 2-L graduated cylinder, thermometer, spare Zip-Loc freezer bags, and multiple ice chests filled with ice. Frozen samples were removed from the freezer and allowed to thaw in a 50° C. oven for a desired amount of time (standard was 20 min). When removed, they were placed on ice to be transported to the shock tube site. Non-frozen samples were also transported on ice.

Once at the shock tube site, the shock tube was lowered into the water bath (approximate dimensions: 28 in×17.5 in×17 in) and it was filled. The top 11 in of the shock tube were not submerged in water. Ice was added to the water bath until the desire temperature was achieved. Additional water was chilled to the desired temperature in the 4-L plastic buckets to be used as sample water. The upper flange of the shock tube was removed; the biomass sample was removed from the ice chest and transferred from the Zip-Loc freezer bag into the shock tube. The appropriate amount of sample water was measured out (typically 1.8 L to bring the total water volume to 2 L). A small amount of the sample water was used to help completely transfer the biomass, and the remaining water was added directly to the shock tube. The gasket was properly centered on the metal flange, the upper section of the shock tube was re-lowered into position, and the eight nuts and bolts around the flange were tightened. The shotgun shell was loaded into the barrel, the firing mechanism was affixed, and the shotgun shell was discharged. The upper flange was unbolted, and the upper section of the shock tube was lifted away. The shocked material was then gathered and filtered through a sieve to remove the lead shot, plastic wadding, and any other non-biological material.

Advantages.

Embodiments of the disclosure may reveal the following features and advantages: the use of a shock on biomass (including lignocellulose and starch-containing grains) may enhance the digestibility of the biomass. Beneficially, the combination of shock treatment in conjunction with biomass pretreatments may occur in either order. Of particular benefit is the combination of shock treatment with alkaline pretreatment performed under specific operating conditions. It is especially beneficial when the combination of shock treatment with alkaline pretreatment includes as the source of alkali a combustor ash.

The mechanical design of the shock apparatus advantageously provides for rapid loading and unloading of biomass slurry. The mechanical design of the shock apparatus also allows for the use of inexpensive fuels (e.g., methane, hydrogen). Other key features include the use of an igniter device (e.g., spark plug) and the optional use of a rupture disk. Benefits of shock treatment are low cost, rapid processing, the ability to shock any particle size, and improved enzymatic yields. For example, shock treatment reduces the amount of enzyme required to achieve a target lignocellulose digestion. Shock treatment greatly enhances the digestibility of lime-treated biomass in a rumen environment. Importantly, the shocked biomass has a high digestibility even thought the particle size is coarse. This is important because fine particles escape the rumen before they have a chance to digest, resulting in low conversion and wasted feed.

While preferred embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. It is within the scope of the disclosure that any of the apparatus embodiments described may be used within any of the methods and processes of the present disclosure, and vice versa.

Where numerical ranges or limitations are expressly stated, such express ranges or limitations should be understood to include iterative ranges or limitations of like magnitude falling within the expressly stated ranges or limitations. The use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, and the like.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the preferred embodiments of the present invention. The inclusion or discussion of a reference is not an admission that it is prior art to the present invention, especially any reference that may have a publication date after the priority date of this application. The disclosures of all patents, patent applications, and publications cited herein are hereby incorporated by reference, to the extent they provide background knowledge; or exemplary, procedural or other details supplementary to those set forth herein.

What is claimed is:

1. A method of making a sugar-based product wherein a lignocellulosic or grain-based biomass is pretreated and sugars are extracted, comprising:
    pretreating the biomass by a process comprising:
        introducing the biomass into a chamber;
        feeding an explodable gaseous mixture into the chamber with the biomass;
        igniting the gaseous mixture in the chamber to detonate it, creating a shock event that produces a shocked biomass;
    transferring the shocked biomass from the chamber;
    converting at least a portion of the shocked biomass into sugars;
    extracting sugars from the shocked, converted biomass; and
    converting at least a portion of the extracted sugars into a sugar-based product.

2. The method of claim 1, further comprising reacting at least a portion of the sugar-based product to produce an alcohol.

3. The method of claim 1 further comprising pretreating the biomass with a chemical before introducing the biomass to the chamber.

4. The method of claim 3, wherein the chemical is an ash material.

5. The method of claim 1 further comprising pretreating the shocked biomass with a chemical after transferring the shocked biomass from the chamber.

6. The method of claim 1, wherein the shock event comprises a time elapse of less than 1 second, and a pressure increase is at least 100 psi.

7. The method of claim 6, wherein the chamber comprises a first end and a second end, each end having an end cap movably attached thereto, wherein each of the end caps comprise a sloped surface configured to assist in rapid opening, closing, and sealing of the covers with the ends, and wherein the shocked biomass is transferred from the chamber by opening the second end and gravitational force.

8. The method of claim 1, wherein the feeding an explodable gaseous mixture into the chamber comprises the gaseous mixture being fed above all of the biomass.

9. A method of making a sugar-based product wherein a lignin-based biomass is pretreated and sugars are extracted, comprising:
    pretreating the biomass by a process comprising:
        introducing the biomass into a high-pressure vessel;
        feeding an explodable gaseous mixture into the high-pressure vessel with the biomass;
        igniting the gaseous mixture in the chamber to detonate it, creating a shock event that produces a shocked biomass;
    transferring the shocked biomass from the high-pressure vessel;
    converting at least a portion of the shocked biomass into sugars;
    extracting sugars from the shocked, converted biomass; and
    converting at least a portion of the extracted sugars into a sugar-based product,
    wherein the shock event comprises a pressure increase of at least 100 psi in less than 1 second of elapsed time.

10. The method of claim 9 further comprising pretreating the biomass with a chemical before introducing the biomass to the high-pressure vessel.

11. The method of claim 10 further comprising pretreating the shocked biomass with a chemical after transferring the shocked biomass from the high-pressure vessel.

12. The method of claim 9 further comprising: pretreating the lignin-based biomass prior to introduction into the chamber high-pressure vessel by adding calcium oxide or hydroxide, water, and an oxidizing agent to the biomass to form a slurry mixture; and oxidizing lignin in the slurry mixture while maintaining the mixture at greater than ambient temperature.

13. The method of claim 9, wherein the feeding an explodable gaseous mixture into the chamber comprises the gaseous mixture being fed above all of the biomass.

14. A method of making a sugar-based product wherein shock pretreatment is used to enhance biomass digestibility and sugars are extracted, comprising:
    pretreating a lignin-based biomass by a process comprising:
        treating the biomass with a chemical to produce a treated biomass;
        introducing the treated biomass into a high-pressure vessel;
        feeding an explodable gaseous mixture into the chamber with the biomass;
        igniting the gaseous mixture in the chamber to detonate it, creating a shock event that produces a shocked biomass;
    transferring the shocked biomass from the chamber;
    converting at least a portion of the shocked biomass into sugars;
    extracting sugars from the shocked, converted biomass; and
    converting at least a portion of the extracted sugars into a sugar-based product.

15. The method of claim 14 wherein the feeding an explodable gaseous mixture into the chamber comprises the gaseous mixture being fed above all of the biomass.

16. The method of claim 14 further comprising: countercurrently washing at least a portion of the shocked biomass with water; and forming a biomass slurry with the wash water and the pretreated biomass.

17. The method of claim 16, wherein the chemical is one of an alkali material, an ash material, or combinations thereof.

18. The method of claim 17 comprising further processing the shocked biomass to produce a biofuel, wherein the shock event comprises a pressure increase of at least 100 psi in less than 1 second.

19. The method of claim 18, wherein the high-pressure vessel comprises a first end and a second end, each end having an end cap removably attached thereto, wherein each of the end caps comprise a sloped surface configured to assist in rapid opening, closing, and sealing of the end caps with the ends, and wherein the shocked biomass is transferred from the high-pressure vessel from opening the second end and gravitational pull.

* * * * *